United States Patent [19]

Han et al.

[11] Patent Number: 5,457,754
[45] Date of Patent: Oct. 10, 1995

[54] METHOD FOR AUTOMATIC CONTOUR EXTRACTION OF A CARDIAC IMAGE

[75] Inventors: Chia Y. Han, Hamilton County, Ohio; David T. Porembka, Boone County; Kwun-Nan Lin, Fayette County, both of Ky.

[73] Assignee: University of Cincinnati, Cincinnati, Ohio

[21] Appl. No.: 725,411

[22] Filed: Jul. 1, 1991

Related U.S. Application Data

[63] Continuation of Ser. No. 561,983, Aug. 2, 1990, abandoned.
[51] Int. Cl.$^6$ ..................................................... G06K 9/00
[52] U.S. Cl. .......................... 382/128; 382/257; 382/266; 382/172
[58] Field of Search .................................... 382/128, 172, 382/264, 266, 257

[56] References Cited

U.S. PATENT DOCUMENTS

| | | | |
|---|---|---|---|
| 4,742,556 | 5/1988 | Davis | 382/51 |
| 5,054,099 | 10/1991 | Wakabayashi | 382/55 |

OTHER PUBLICATIONS

Olaf T. von Ramm, Ph.D. et al.; "Cardiac Imaging Using a Phased Array Ultrasound System"; *Circulation;* pp. 258–261; Feb., 1976; USA.
Joseph Kisslo, M.D., et al.; "Cardiac Imaging Using a Phased Array Ultrasound System"; *Circulation;* pp. 262–267; Feb., 1976; USA.
James F. Havlice et al.; "Medical Ultrasonic Imaging: An Overview of Principles and Instrumentation"; *Proceedings of the IEEE;* pp. 620–641; Apr., 1979; USA.
J. Ophir et al.; "Digital Scan Converters in Diagnostic Ultrasound Imaging"; *Proceedings of the IEEE;* pp. 654–664; Apr., 1979; USA.
John G. Abbott et al.; "Acoustic Speckle: Theory and Experimental Analysis"; *Ultrasonic Imaging;* Sep., 1987; pp. 303–324; 1979; USA.
Paul F. Moynihan, B.S. et al.; "Quantitative Detection of Regional Left Ventricular Contraction Abnormalities by Two–Dimensional Echocardiography"; *Circulation;* pp. 752–760; Apr., 1981; USA.
Alfred F. Parisi, M.D. et al.; "Quantitative Detection of Regional Left Ventricular Contraction Abnormalities by Two–Dimensional Echocardiography"; *Circulation;* pp. 761–767; Apr., 1981; USA.
Ernest Garcia, Ph.D. et al.; "Real Time Computerization of Two–Dimensional Echocardiography"; *American Heart Journal;* pp. 783–792; Jun., 1981; USA.
Joseph W. Helak, M.D. et al.; "Quantitation of Human Left Ventricular Mass and Volume by Two–Dimensional Echocardiography; In Vitro Anatomic Validation"; *Circulation;* pp. 1398–1407; Jun., 1981; USA.
David J. Skorton, M.D. et al.; "Digital Image Processing of Two Dimensional Echocardiograms: Identification of the Lendocardium"; *The American Journal of Cardiography;* pp. 479–486; Sep., 1981; USA.
Peter Alexander, "Array Processors in Medical Imaging"; *IEEE Computer;* pp. 17–30; Jun., 1983; USA.
Andrew J. Buda, M.D. et al.; "Automatic Computer Processing of Digital 2–Dimensional Echocardiograms"; *The American Journal of Cardiology;* pp. 384–389; Aug., 1983; USA.

(List continued on next page.)

Primary Examiner—Leo H. Boudreau
Assistant Examiner—David R. Anderson
Attorney, Agent, or Firm—Frost & Jacobs

[57] ABSTRACT

An improved method is provided for extracting the edge boundary of an object presented as an ultrasound video image, in particular the edge boundary of the LV of the heart, which includes preprocessing algorithms, contour extraction algorithms and knowledge based contour following algorithms.

26 Claims, 13 Drawing Sheets

OTHER PUBLICATIONS

Werner Zwehl, M.D.; "Validation of a Computerized Edge Detection Algorithm for Quantiative Two–Dimensional Echocardiography"; *Circulation;* pp. 1127–1135; Nov., 1983; USA.

Steve M. Collins, Ph.D. et al.; "Computer–Assisted Edge Detection in Two–Dimensional Echocardiography: Comparison with Anatomic Data"; *The American Journal of Cardiology;* pp. 1380–1387; May, 1984; USA.

Liang–Fu Zhang et al.; "An Effective Algorithm for Extracting Serial Endocardial Borders from 2–Dimensional Echocardiograms"; *IEEE Transactions On Biomedical Engineering;* pp. 441–447; Jun. 1984; USA.

K. Hwang; "Structure and Algorithms For Array Processors"; *Computer Architecture and Parallel Processing;* pp. 325–333; 1984; USA.

Andrew J. Buda et al.; "Digital Two–Dimensional Echocardiography"; *Digital Cardiac Imaging;* pp. 156–181; 1985; USA.

David J. Skorton et al.; "Digital Image Processing and Analysis in Echocardiography"; *Cardiac Imaging and Image Processing;* pp. 171–205; 1986; USA.

Rene Stolk; "Calculating the Area of an Irregular Shape"; *Byte;* pp. 135–136; Feb., 1987; USA.

Dan Adam et al.; "Semiautomated Border Tracking of Cine Echocardiographic Ventricular Images"; *IEEE Transactions On Medical Imaging;* pp. 266–271; Sep., 1987; USA.

A. Herment et al.; "Limitations of Ultrasound Imaging and Image Restoration"; *Ultrasonics;* pp. 267–273; Sep., 1987; USA.

Edwin R. Wolfe; "Accuracy of Automatically Determined Borders In Digital Two–Dimensional Echocardiography Using A Cardiac Phanton"; *IEEE Transactions On Medical Imaging;* pp. 292–296; Dec., 1987; USA.

R. C. Gonzalez et al.; "Digital Image Processing"; pp. 354–369; 1987; USA.

Author Unknown, "Data Translation Co. Catalog"; pp. 2–47 through 2–70; 1987; USA.

P. K. Sahoo; "A Survey of Thresholding Techniques"; *Computer Vision, Graphics, and Image Processing;* pp. 233–260; 1988; USA.

Liqun Wan; "Extraction of Heart Ventricle Contours from Echocardiographic Images"; pp. 1–12; Oct., 1989; USA.

H. G. Bosch et al.; "Automated Contour Detection on Short–Asix Transesophageal Echocardiograms"; *Transesophageal Echocardiography;* pp. 253–259; 1989; Country unknown.

Philip J. Currie, M.D.; "Tee: Current Applications and Future Directions"; *Cardiology;* pp. 57–62, 69, 133; Mar., 1990, USA.

John H. Urbanowicz, M.D. et al.; "Comparison of Transesophageal Echocardiographic and Scientigraphic Estimates of Left Ventricular End–Diastolic Volume Index and Ejection Fraction in Patients Following Coronary Artery Bypass Grafting"; *Anesthesiology;* pp. 607–612; 1990; USA.

A. Christian Held, M.D. et al.; "Automatic Echocardiographic Analysis: Use of an Artificial Intelligence Approach"; p. 1; date unknown; USA.

$$SOBEL = |A+2B+C-G-2H-I| + |C+2F+I-A-2D-G|$$
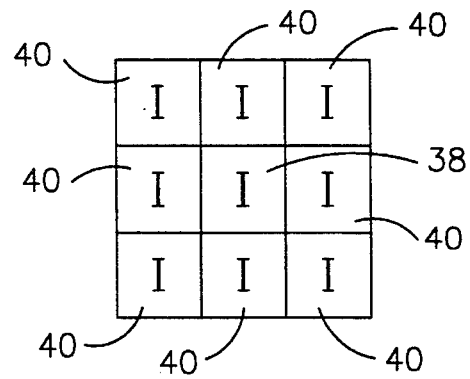
FIG. 5
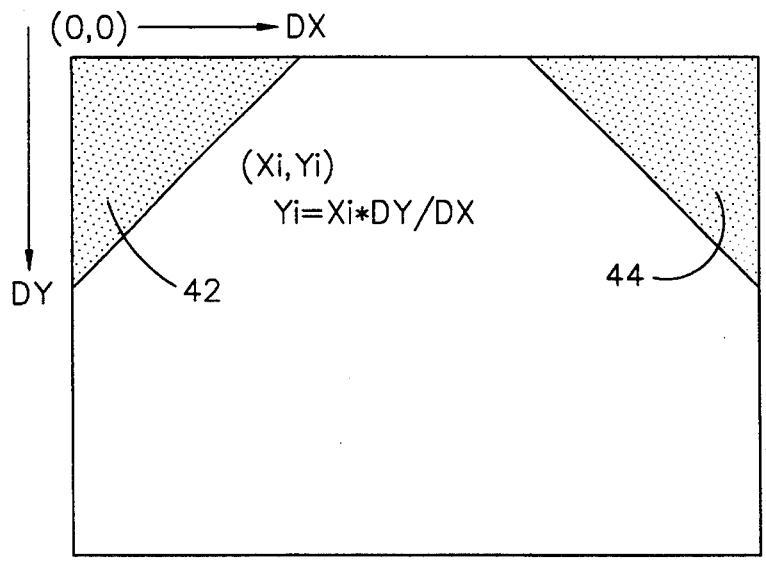
FIG. 6
FIG. 7

. O .
O X O
. O .

```
X . . . X . . . X
. . . . . . . . .
. . . . . . . . .
. . . . . . . . .
X . . . X . . . X
. . . . . . . . .
. . . . . . . . .
. . . . . . . . .
X . . . X . . . X
```

———— : CORRECT INTERPOLATION
------ : INCORRECT INTERPOLATION (1 Microfiche, 49 Pages)

METHOD FOR AUTOMATIC CONTOUR EXTRACTION OF A CARDIAC IMAGE

This application is a continuation of Ser. No. 07/561,983 Aug. 02, 1990 abandoned.

This application incorporates by reference the computer program contained in the microfiche appendix appended hereto, consisting of 1 microfiche having 49 frames.

TECHNICAL FIELD

The present invention relates generally to a method for automatically determining boundary locations of an object presented in a video image, and is particularly directed to the extraction of boundary contours of the left ventricle of the heart in a transesophageal echocardiographic ultrasonic image. The invention will be specifically disclosed in connection with an automated boundary extraction system which uses knowledge about the heart anatomy and echocardiographic imaging to guide the selection of an image processing methodology for thresholding, edge detection, and contour following. The method includes the elimination of noise images by appropriate filters implemented at various stages during the process to minimize the chances of false contour identification.

BACKGROUND OF THE INVENTION

The use of two dimensional echocardiography imaging of the heart is an important noninvasive procedure in clinical cardiology. In particular, the endocardiac boundary of the two dimensional echocardiography image taken at the mitral valve level of the left ventricle (LV) of the heart, the short axis view, has been used for providing quantitative information about various cardiac functions such as the pressure-volume ratio, the ejection fraction, and cardiac wall motion. To quantify these functions, the contour of the LV needs to be first extracted and its cross-sectional area computed. Recently, the use of transesophageal echocardiography (TEE) has provided new apparatuses and methods for obtaining better quality images.

The problem of contour extraction based on two dimensional ultrasonic sector scans of any image, and in particular of the LV, is a difficult digital image processing problem because the images have very low spatial resolution, high levels of speckle noise, and, frequently the absence of an edge signal on some boundary conditions of the myocardial contour.

The prior art has identified four factors which affect the processing of images. First, the main component of image distortion is caused by the nonuniform reflection of the ultrasound beam from different parts of the body. The boundary angle relative to the ultrasound beam affects the reflective energy. For instance, the boundaries on the right and left side are often unclear because they are almost parallel to the ultrasound beam. Second, if an organ is in close proximity to a chamber or other object of interest, it may appear to be connected to that object. For example, in examining the heart, the papillary muscle sometimes appears as though it is connected to the wall, and sometimes as though it is not. Third, as mentioned above, speckle noise affects the processing of images. It is the main noise source in two dimensional echo images, and is caused by the nonfocused beam of the ultrasonic transducer and the nonhomogeneous tissue structure of the body. Lastly, improper system calibrations can result in poor quality. This may generate a picture which is too bright or dark because of biasing error in the analogue circuit-mesh like lines which may appear on ultrasonic images are caused by improper sampling.

In general, the current contour detection schemes for contour extraction of the LV ultrasound image can be classified into three groups based on the processing strategies used. The first strategy is edge based. It consists of applying an edge operator to the ultrasound image and selecting a proper threshold value to determine the edge points. Several major stumbling blocks have to be successfully overcome when using this strategy. The first stumbling block is that the edge based strategy inherently involves the difficult problem of finding a proper threshold value. When a good threshold value is selected and all of the edges are extracted, there remains the additional problem of tracking all of the relevant edges which correspond to the LV boundary, and thereafter forming a closed contour from the boundary segments.

The second major strategy is region based or center based. The center of the region which corresponds to the LV cavity center is used to derive radial lines equally spaced in angles. A single boundary point is searched along each radial line. Filtering and interpolation methods are used to eliminate incorrect boundary points and to interpolate the closed contour. The center based method has the advantage of reducing the boundary searching problem from two dimensions to only one dimension.

Three problems can readily be identified with the region based or center based strategy. The first problem is finding the center of the LV automatically. This problem requires adequate region segmentation procedures which are not simple due to the low contrast and high noise content of the signal. Simple thresholding schemes do not yield satisfactory results. Therefore, the center is normally located manually by a human operator with a pointing device.

The second problem is that the region based or center based strategy cannot find the correct boundary points when the contour is not all convexed or protrusions are formed on the boundary. The concavity of the contour will cause a problem because a single point per radial line is normally assumed. This approach cannot find a boundary point correctly if the contour is nearly parallel to the radial line wherein multiple points along a radial line may belong to the boundary contour. In the short axis LV images, there are protrusions on the LV boundary due to the trabeculation and the papillary muscles. The two major protrusions normally correspond to the papillary muscles of the LV. The concave curve on the contour, formed by the papillary muscle, is referred to herein as a cave. The presence of such a cave means that the radial line may intersect with the boundary at two additional points.

A third problem with the region based or center based strategy is that radial line search scheme is very noise sensitive. Because of this, it is difficult to identify and delete erroneous boundary points caused by the "noisy blobs" within the region.

The third strategy is sequential frame based. Boundary contours are determined by providing a reference contour outline first by human operator. This strategy offers improved reliability by using statistical information of sequential frames. However, the methods of this type still rely on manual operation on either one or several frames.

Filtering and noise deletion is important to the proper operation of this system. However, improvements in the quality of the ultrasonic image and signal from the ultrasonic transducer, or enhancements within the ultrasonic system, will reduce the need for filtration or smoothing.

Thus, the prior art indicates that the determination and extraction of relevant image points such as region points, the region center, or the boundary points has proved to be very difficult. Semi-automatic methods rather than fully automated methods have been used because the two dimensional echocardiography LV images lack boundary signals in certain portions of the image, and have high noise content. There is a need in the art for a system which can automatically and reliably determine and extract features of an imaged object, and in particular the boundary contour of the left ventricle of the heart, on a real time basis, even in the presence of poor imagery. The method should also provide information which may be used in quantitative analysis of the boundary.

SUMMARY OF THE INVENTION

Accordingly, it is an object of the present invention to provide a method for quickly and reliably extracting a feature of an object presented as a video signal or image.

It is another object of the present invention to provide a method for extracting the boundary edge of the LV chamber of the heart on a real time basis.

It is yet another object of the present invention to provide a method for extracting the boundary of the LV in a manner which provides information for quantitative analysis of the LV.

It is still another object of the present invention to provide a method for extracting the boundary location of an imaged object based on knowledge of the shape of that object, and on observations of previously processed images thereof.

It is another object of the present invention to provide a method for automatically determining a threshold value for pixel intensity of a video signal or image.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein, an improved method is provided for extracting the edge boundary of an object presented as an ultrasound video image, in particular the edge boundary of the LV of the heart, which includes preprocessing algorithms, contour extraction algorithms and knowledge based contour following algorithms. The method includes digitizing and storing a video signal, followed by applying a low pass filter mask to remove speckle noise. Unneeded data is eliminated from consideration and a reduced size feature picture is generated based on the maximum intensity difference of the original pixels. A low pass horizontal filter is thereafter applied to remove scanning noise. A threshold value is determined for the feature picture, and the data points are assigned new intensity levels based on their original intensity in comparison to the threshold level. Noise is deleted from the data by determining the size of various regions of given intensities, and resetting the intensity of data points within certain of those regions based on the size of the regions. The center point of the largest region of a given intensity is determined by locating geometric shapes centered at grid points, subject to specific rules to limit the placing of such geometric shapes to the internal region of the LV. The feature picture is enhanced through localized thresholding based on the original picture. The internal region thusly determined is dilated by adding layers to its boundary. The edge of the boundary is detected, and the contour closed by analyzing the radial distance to the internal region boundary along radial lines emanating from the center of the internal region, and thereafter interpolating the data points based on knowledge of the image. The results are smoothed, and then mapped from the feature picture back to the original picture. Boundary points are determined along radial lines emanating from the center on the original picture which fall within a given region of the boundary established in the feature picture. A filter may be applied to the resulting edge, and the internal area may be calculated based on the extracted boundary.

Still other objects of the present invention will become apparent to those skilled in this art from the following description wherein there is shown and described a preferred embodiment of this invention, simply by way of illustration, of one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 5 illustrates the Sobel operator.

FIG. 6 diagrammatically illustrates a 3 pixel by 3 pixel mask used for filtering.

FIG. 7 illustrates the triangular regions of the window which are deleted.

Reference will now be made in detail to the present preferred embodiment of the invention, an example of which is illustrated in the accompanying drawings.

DETAIL DESCRIPTION OF THE PREFERRED EMBODIMENT

Figure 1:
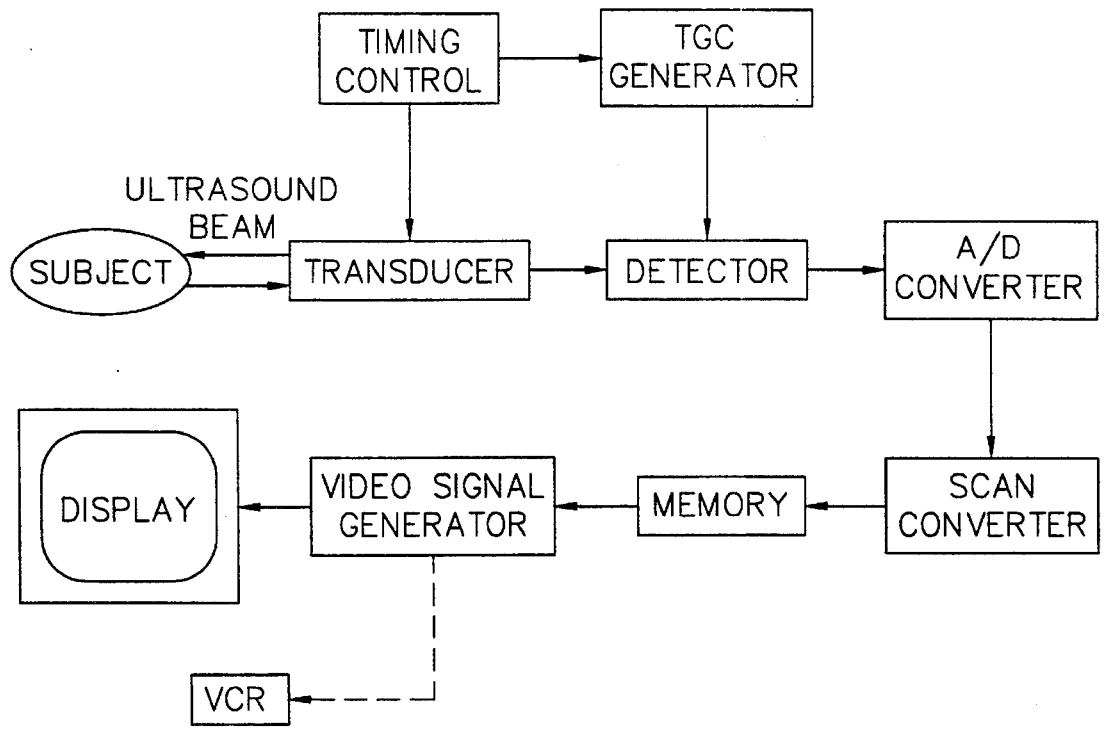
FIG. 1 is a diagrammatic view of a typical two-dimensional ultrasound imaging apparatus.

Referring now to the Figures, FIG. 1 shows a block diagram of a typical two dimensional ultrasound echo apparatus. The components and operation of the apparatus shown in FIG. 1 are well known in the prior art and are utilized to generate the ultrasound image which can be analyzed in accordance with the methods of the present invention. Improvements and changes in the image generating device, which enhance an image delivered for analysis in accordance with the present invention will not interfere with the application of the methodology of the present invention, but rather will allow the present invention to operate more efficiently. It is possible with sufficient improvement in the quality of the ultrasound image delivered by such apparatuses that some of the steps of the method of the present invention may be modified or deleted while still producing the desired extraction of the object boundary. Other methods of producing an image, such as magnetic resonance, may also be utilized to produce an image for processing in accordance with the present invention.

Figure 2:
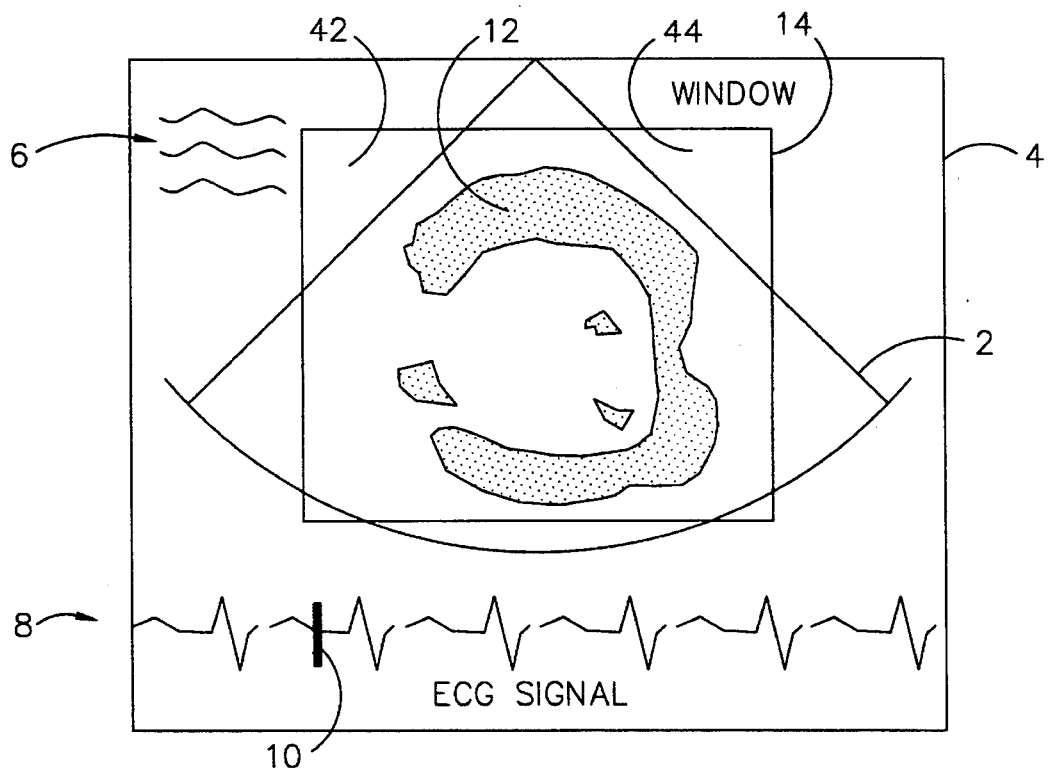
FIG. 2 is a diagrammatic illustration of a typical display generated by the apparatus of FIG. 1.

FIG. 2 diagrammatically illustrates a typical display delivered to the display or VCR by the apparatus indicated in FIG. 1. It will be noted that the display includes a digitized sector or pie shape ultrasound image 2 shown on a screen 4 which consists of individual pixels. The most common resolutions for screen 4 are 512 pixels×512 pixels, 640 pixels×480 pixels and 256 pixels×256 pixels. The digitized image quality is dependent not only on the resolution of the whole image, but also on the resolution of each pixel, expressed as a number of gray levels per pixel. A black and white pixel is usually digitized into eight bits, i.e. 256 gray levels per pixel ranging from an intensity of 0 to an intensity of 255. Colored pixels may be digitized into 16 or 24 bits. A typical configuration of the image acquisition, storage and display capability of an apparatus as shown in FIG. 1 is capable of handling data at a very high rate, because the video signal contains 30 frames per second.

Screen 4 typically also includes identifying indicia or medical data not produced by the ultrasonic transducer. Such additional information would include written indicia 6 located in the upper left corner (or anywhere else) of screen 4, as well as ECG signal 8 at the bottom of screen 4. Marker 10 transverses screen 4 horizontally along ECG signal 8 to indicate current cardiac pulses.

Within ultrasound image 2 lies the particular feature 12 from which the boundary edge is to be extracted for analysis. In the specific application of the preferred embodiment of the present invention, feature 12 is a short axis view or-the left ventricle (LV) of the heart using transesophageal echocardiography techniques well known in the industry. Information displayed on screen 4 outside of ultrasound image 2 represents data which is not necessary or desired in order to process LV 12. Window 14 is not a part of the output of the ultrasonic imager of FIG. 1, but rather is a step in applying the methods of the present invention which will be described later.

Figure 3:
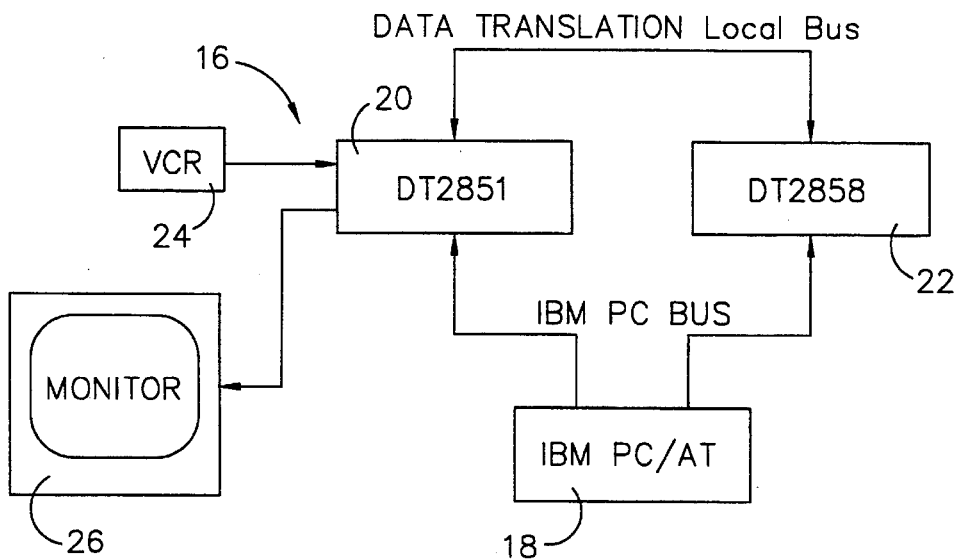
FIG. 3 is a block diagram of the hardware utilized in practicing the methods of the present invention.

Referring now to FIG. 3, there is shown a block diagram of the image system 16 utilized in practicing the methods of the present invention. The main hardware includes a computer 18, such as an IBM PC/AT, two commercially available image boards 20 and 22, made by Data Translation Company of Marlboro, Mass., a VCR 24 and a video monitor 26. The IBM PC/AT 18 used is a 6 MHZ machine based on the 80286 CPU. The image boards 20 and 22 are plugged in its expansion slots. One image board 20 is the primary image board, a DT 2851, and the other image board 22 is the coprocessor board, a DT 2858. The primary image board 20 is a 512×512×8 bit frame grabber. It can only digitize a black and white signal. An onboard notch filter can remove the color component in the event that a color video signal is delivered to the system 16. Color is not utilized in the preferred embodiment of the present invention due to additional computational time necessary, although it may be easily incorporated with a computer processor unit having sufficient speed while still practicing the methodology of the present invention.

The coprocessor board 22 is a pipelined frame processor. It can do mass convolution, zoom, pan, scroll, histogram, logic and arithmetic operations. It includes special purpose hardware which greatly reduces the time required to perform repeated operations. For example, it can do 2.5 million multiplications per second. For a 3×3 mask convolution on a 512×512 image, the coprocessor board is 250 times faster than the IBM PC/AT software operation.

A video signal of the two dimensional image may be prerecorded on a tape and delivered to system 16 by playing the tape on VCR 24. Alternatively, the image may be delivered directly from the video signal generator of the apparatus illustrated in FIG. 1. Additionally, the actual signal delivered to system 16 may, with the incorporation of suitable hardware and interfacing software, be the actual sector shape ultrasound image 2 illustrated in FIG. 2. This would eliminate the need to delete the ancillary information sent to the display or VCR, as mentioned above. The incoming video signal is initially digitized and filtered by system 16. The results may be displayed on video monitor 26.

The method of the present invention incorporates knowledge about the heart anatomy, data acquisition and processing for guiding the usage of both edge and center based image processing methodologies. Both localized and global information are used to generate the desired contour following scheme. Global information is used to derive the rough shape of the LV chamber and to delete noise due to many different sources. Also, knowledge is used to obtain the correct boundary and to avoid fatal errors caused by noise. The method can be divided into three major steps. They are preprocessing, contour extraction, and knowledge based contour following.

Preprocessing is used to reduce the noise and the computational requirements. This is especially advantageous in processing the present day echocardiographic image wherein there is a large amount of noise, and the application requires that the result be generated in a very short time period so that it can be used in operating room environments. The preprocessing includes both noise reduction operations and data conversion procedures.

The contour extraction stage includes four major steps. They are automatic threshold selection for the feature picture, LV region segmentation and center finding, localized thresholding, and region based contour curve generation. As will be described in detail below, the processing steps are performed on a feature picture which is one-ninth of the original picture size in order to improve efficiency and speed.

The knowledge based contour following stage utilizes knowledge to provide a mechanism for either recognizing or recovering from failure in the information extraction process. This stage includes region based contour curve generation and knowledge based contour manipulation, followed by a search for the real boundary points based on the processed information.

Returning now to the preprocessing stage, the object at this point is to reduce the noise present in the video signal and to reduce the computational requirements in order to speed up the processing. The noise reduction is accomplished through linear or nonlinear filter masks which can be done by the coprocessor board 22. The data reduction or conversion eliminates unwanted, unnecessary raw data which is not useful in performing the automated edge extraction. Preprocessing includes low pass filtering, computation of the pie shape ultrasonic image, windowing, background deletion, feature picture creation and second low pass filtering.

During the preprocessing stage, a three pixel by three pixel low-pass filter is used to smooth the entire image. The filter is diagrammatically illustrated at FIG. 6. As is well-known, each pixel within the image is averaged with its eight neighbors. In FIG. 6, the pixel being averaged by the filter procedure is the center pixel 38 which is surrounded by its eight neighbors 40. As used herein, and in the claims, the eight neighbors of a given pixel refer to the immediately adjacent pixels as illustrated in FIG. 6. The gray scale of all nine pixels are summed and divided by nine. The central pixel 38 is then assigned the resulting gray scale level. Although as a result of this low-pass filter procedure the picture becomes somewhat blurred, it is extremely helpful in removing speckle noise from the image. This step is very important because the image cannot be processed with the existence of high level speckle noise. The filter is accomplished by coprocessor 22, and takes less than one second to complete. Median filters, as also known in the industry, may get rid of speckle noise without burring the image, but take significantly more time to process because such filter procedures cannot be done by coprocessor 22.

Two dimensional ultrasound images are produced in sector form, as described above. As also mentioned above, the background outside of the pie shape does not include any useful data. This background may cause fatal errors in the processing and edge extraction, and unnecessarily complicates the computations. It is desirable to consider only the data within the sector. It is therefore necessary to determine the sector shape.

Figure 4A:
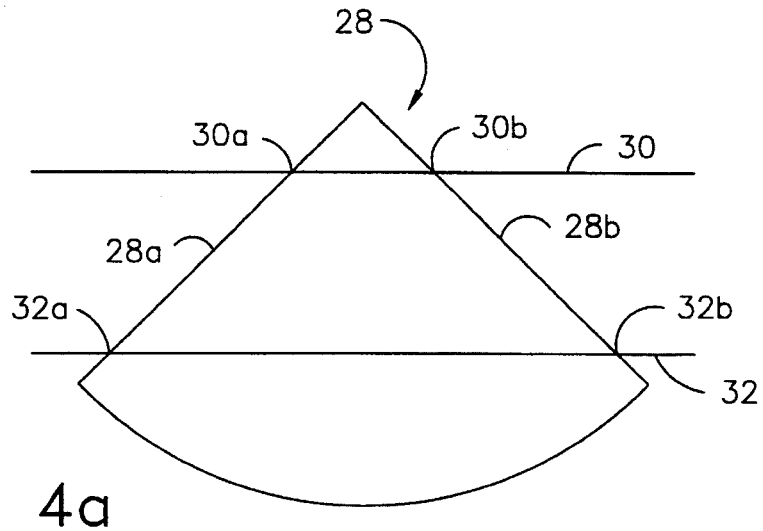
FIGS. 4a and 4b diagrammatically illustrate the sector shape and horizontal lines used to determine the edges of the sector.
Figure 4B:
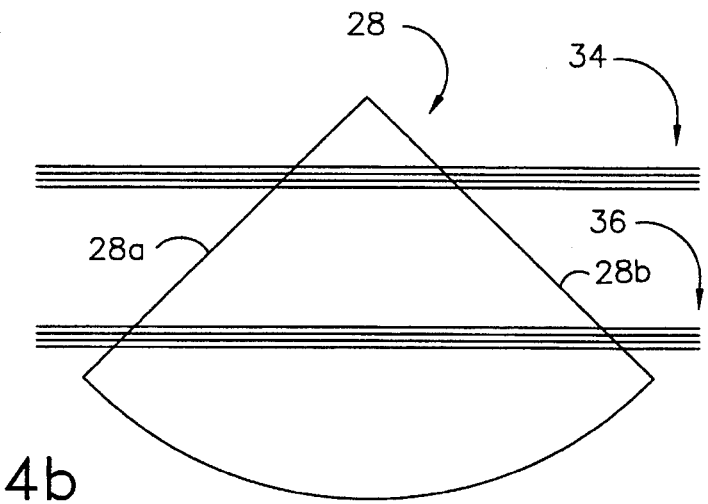

Referring now to FIGS. 4A and 4B, there is shown the sector shape, generally indicated at 28. In order to define the sector shape 28, the side edges 28a and 28b need to be determined. One way of determining the location of edges 28a and 28b is to find the intersections 30a, 30b, 32a and 32b of two spaced apart horizontal lines 30 and 32. Lines 30 and 32 are spaced as far apart as is practical and still be guaranteed to intersect both of the edges 28a and 28b. In order to find these intersections 30a, 30b, 32a and 32b correctly, the gray level changes along the respective horizontal lines 30 and 32 are examined using a Sobel operator. A Sobel operator is illustrated at FIG. 5 along with the formula which gives the value of the Sobel operator for the center pixel 37 of the 3×3 pixel region. As is well-known, variables A through I represent the gray scale value of the respective pixels. Once the four edge points, 30a, 30b, 32a and 32b are determined, edges 28a and 28b may be mathematically calculated as determined by the respective pair of two points, 30a and 32a, and 30b and 32b.

The intersection points of horizontal lines 30 and 32 with edges 28a and 28b are not always well defined. In order to increase the reliability of defining the edges 28a and 28b, a group of lines is used in the preferred embodiment. Each group includes 4 lines which are closely spaced, although the two groups 34 and 36 are spaced far apart. Each group includes four intersections with each edge 28a and 28b. The location of each intersection point, sixteen in total, in determined according to the Sobel operator as described above. Within each group of four intersections, the three intersections which have been identified as lying closest to each other are averaged to produce one intersection point. To determine the three closest points, the distances between a given point and each of the remaining three are determined and summed. The process is repeated for all of the points within the same group at the same edge. The point which has the highest total is the point which is considered the farthest from the other three points. This point is no longer considered. This yields a total of four intersection points, two on each edge 28a and 28b. The edges may then be mathematically determined based on the two sets of two points. The utilization of two groups of lines 34 and 36 greatly reduces the possibility of the incorrect selection of the intersection point.

Only the side edges 28a and 28b of the sector 28 are determined. The arc of the sector is not examined, in favor of a computational time, since most of it lies outside of the chosen window as described below.

Referring again to FIG. 2, the area of the sector image, 2, is approximately half of the area of screen 4. The feature of interest 12, i.e. the LV, comprises only a small part of the sector. During the preprocessing stage, a window 14 is defined so that it is large enough to contain the feature 12, but small enough so that it does not contain more pixels than is necessary to perform the operation. In the preferred embodiment, a predefined window of 270 pixels horizontally and 225 pixels vertically is centered in a predetermined position generally about the expected location of feature 12. In the preferred embodiment, this window can be redefined by the operator if the LV 12 is consistently outside of the predetermined window. For most cases, the predetermined default window position and size may be used. The image data contained within the selected window is stored in the main memory of computer 18. The use of the window not only reduced the number of pixels being processed, but simplifies the processing by inherently eliminating most of the background.

As shown in FIG. 2, there are two triangular regions 42 and 44 which lie within window 14 but outside of sector 2. These triangular regions 42 and 44 are part of the background and do not contain any useful or necessary information. Therefore, during the preprocessing stage, these triangular regions 42 and 44 are deleted from consideration. Referring to triangular region 42, it being recognized that the analysis thereof is similar to the analysis of triangular region 44, the two sides DX and DY as indicated in FIG. 7 can be computed by the side edge line function and the window boundary as determined above. Every point on the triangular region can be computed by the formula $Y_i = X_i \times DY/DX$, for each point $(X_i, Y_i)$. As indicated, this calculation needs one multiplication and one division for every point considered. However, a digital differential analyzer (DDA) can compute every point on the line without any multiplication or division. The DDA algorithm is as follows:

Step 1: N=DX; P=0;

Step 2: Delete the first N pixels in this line;

Step 3: P=P+DX;

Step 4: IF (P>=DY) THEN (P=P−DY; N=N−1;)

Step 5: Repeat step 4 until P<DY

Step 6: Process next line on the picture

Step 7: Repeat steps 2–6 until N<=0

The use of the DDA is important, since multiplication and division take a much longer time. The DDA therefore reduces the total processing time.

After the window is selected and the background is deleted, the window is subdivided into non-overlapping blocks of three pixel by three pixel size. A reduced image, referred to herein and in the claims as the feature picture is formed by mapping each block of nine pixels of the original picture in window 14 into a single point in the feature picture, thereby producing a feature picture of 1/9 the size of the initial window of the original picture. A gray scale value is assigned to each single pixel of the feature picture which is equal to the difference between the maximum and minimum gray scale values of the nine pixels which comprise the three pixel by three pixel block that the respective single pixel in the feature picture represents. Thus, if all nine pixels within a single block have the same gray scale value, such as all are black (0) or all are white (255), the difference is zero yielding a black corresponding single point in the feature picture. This mapping operation is basically a non-linear edge operator. This method can be used only after the speckle noise has been removed from the image, as described above. Although other edge operators may also be utilized, this operator was developed and found to be computationally faster than a Sobel edge operator.

Due to the nature of the line scan sampling, the maximum differences often occur between scan lines and not between columns, causing horizontal streaks to be formed in the feature picture. A one pixel by three pixel low-pass filter is applied to eliminate this effect. As is known with respect to filters, the gray scale value of the center pixel of three pixels within the filter mask is set equal to the average gray scale level of the three pixels.

According to the preferred embodiment of the present invention, all processing, prior to searching for the actual boundary within the original window, is done on the feature picture. This increases the speed of processing by at least nine times with respect to the time it would take to process the original window, since the feature picture is only 1/9 the size of the original window. The resulting faster processing time makes the use of the method of the present invention practical in clinical settings.

As identified above, the next stage of the method of the present invention is contour extraction, which includes four steps. The first step is the automatic selection of a threshold level for the feature picture. Thresholding is one of the most important methods in segmentation because it transforms a picture of multiple gray scale levels into a binary picture, i.e. with only two gray levels. As used herein, a "binary" picture may in fact contain more than two gray levels, wherein the multiple gray levels are used to reflect information other than intensity, such as region labeling, etc.

In analyzing the ultrasound image of the left ventricle, it is desirable to identify the internal region of the left ventricle. Since the two-dimensional ultrasound image displays the left ventricle as a dark area, the thresholding step distinguishes the dark area which represents the internal region from the other lighter areas.

Figure 8:
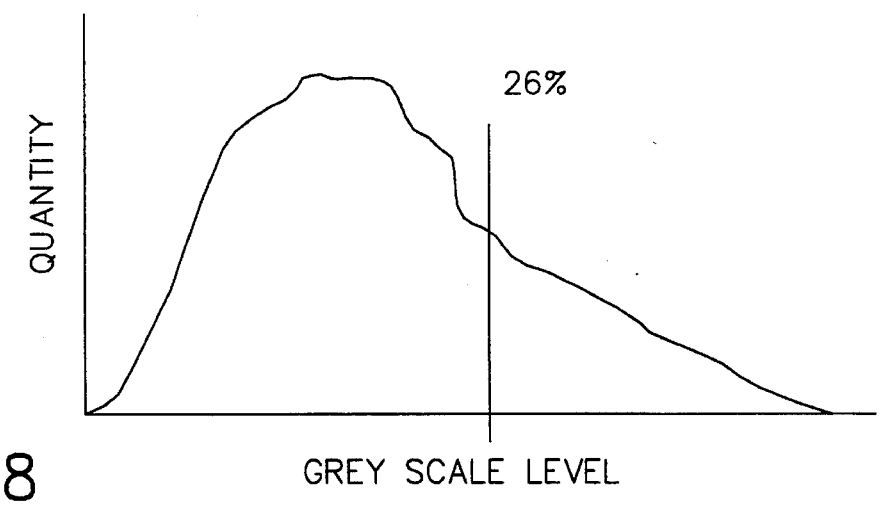
FIG. 8 is a histogram of all points of the feature picture.
Figure 9:
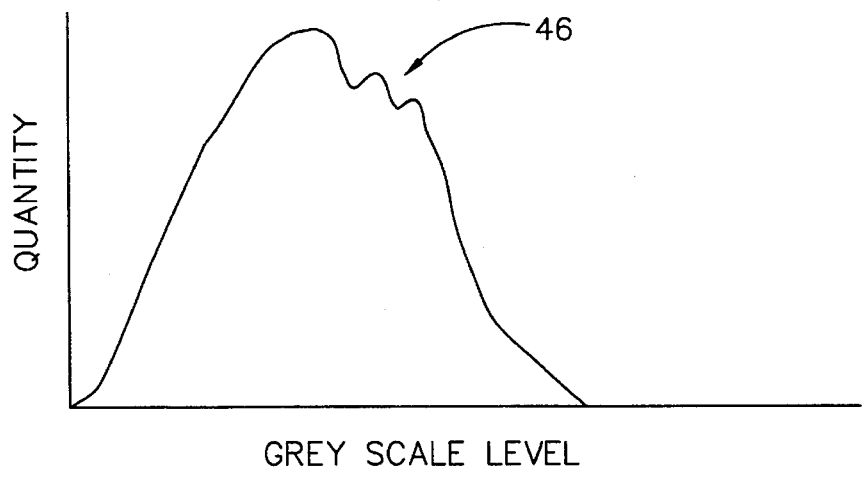
FIG. 9 is a histogram of the remaining points of the feature picture after the 26% brightest points and their 8 neighbors are removed from consideration.

The threshold selection method of the present invention begins with the computation of a histogram of the feature picture as indicated at FIG. 8. The horizontal scale of the histogram represents the 256 different gray scale levels which a pixel within the feature picture may have at this point in the processing. The vertical scale represents the total number of pixels which have the corresponding gray scale level. After this histogram is computed, the feature picture pixels which correspond to the top 26% of the histogram are identified or "marked". These pixels correspond to the brightest 26% of the pixels in the feature picture. Next, for each pixel so marked, its eight adjacent neighbors are also marked.

Next, a second histogram is computed based on the feature picture pixels which have not been marked during the previous steps. The resulting graph represents the histogram of the darker pixels of the feature picture. Based on the knowledge of the picture, these darker pixels generally correspond to the internal region of the LV, which is of interest in the preferred embodiment. It is possible that the second histogram may include localized humps in the graph generally illustrated at 46. The histogram is smoothed to minimize the humps.

Figure 10:
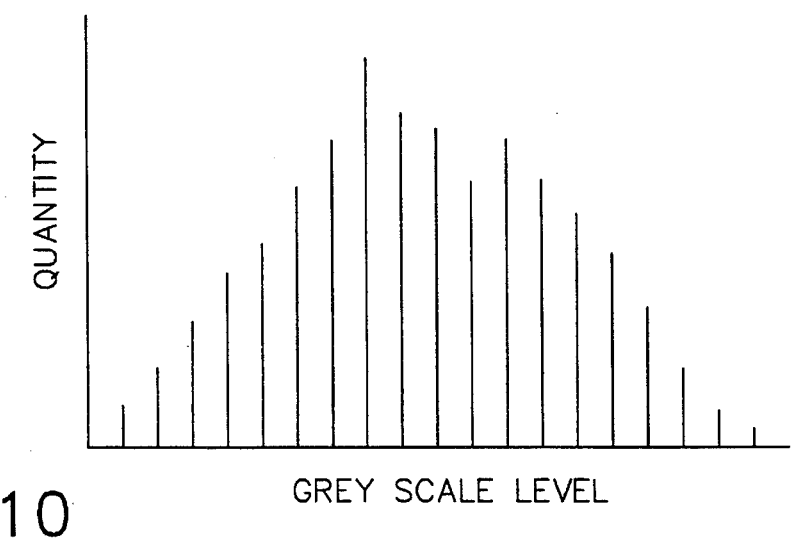
FIG. 10 is a histogram illustrated as a bar graph.

Smoothing the second histogram is accomplished by averaging each set of adjacent five points, as more clearly illustrated in FIG. 10. The histogram of FIG. 10 is shown as a bar graph where the height of the bars are equal to the quantity of pixels having the specific gray scale level for that bar. The histogram is smoothed for each bar by averaging its height with the heights of the two bars on either side of it. The subject bar is then assigned a new height or quantity, which is equal to the average height.

Figure 11:
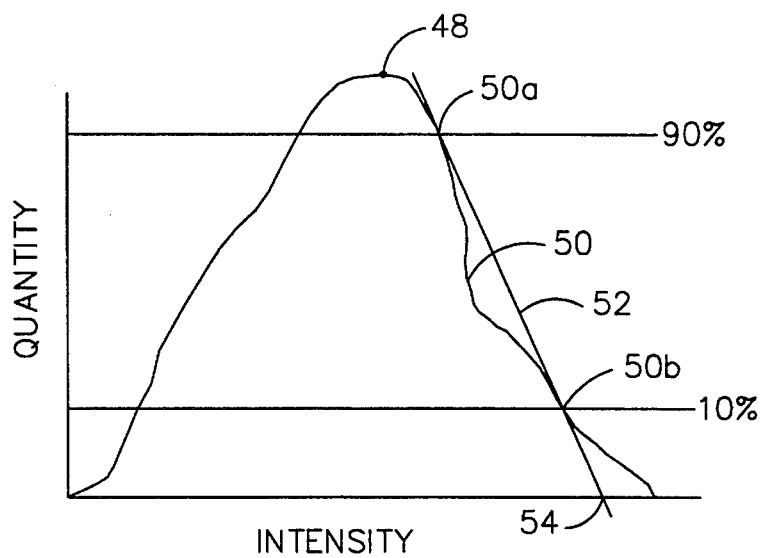
FIG. 11 is a histogram showing the 90% and 10% points for determining the feature picture threshold.

Once the second histogram has been smoothed, the peak value of the curve is determined, indicated by point 48 in FIG. 11. Horizontal lines are then "drawn" which are equivalent to 90% and 10% of the peak value of the histogram. The points along the descending side of the curve

50 which have a quantity value corresponding to 90% of the quantity of point 8, indicated at point 50a, and corresponding to 10% of the quantity value of point 48, indicated at point 50b, are identified. A line 52 is mathematically computed which passes through points 50a and 50b. The threshold value is thereafter selected as the gray scale level value at the point 54 where line 52 intersects the horizontal axis.

The thusly calculated threshold value is then used to generate a binary image of the feature picture, by setting all points within the feature picture which have a gray scale level greater than the threshold level equal to a first predetermined gray scale level. All points whose gray scale level are less than the threshold value are equal to a second predetermined gray scale level.

In the preferred embodiment, the points with a gray scale level which exceeds the threshold value are most likely not part of the interior region of the LV. For later processing, the first predetermined level is set at less than 255. The second predetermined level is set at zero.

This two histogram threshold selection algorithm was selected because a single histogram can only provide global information based on all of the points. However, with two-dimensional images, it is practically impossible to select a threshold level based on all of the points that will effectively separate the internal LV chamber region from the surrounding parts. Thus, the present method for selecting the threshold emphasizes the dark center which corresponds to the internal region of interest by eliminating the brighter points from consideration. This is done by discarding the 26% brighter points and their neighbor points from the computation of the second histogram from which the threshold level was selected.

Figure 12:
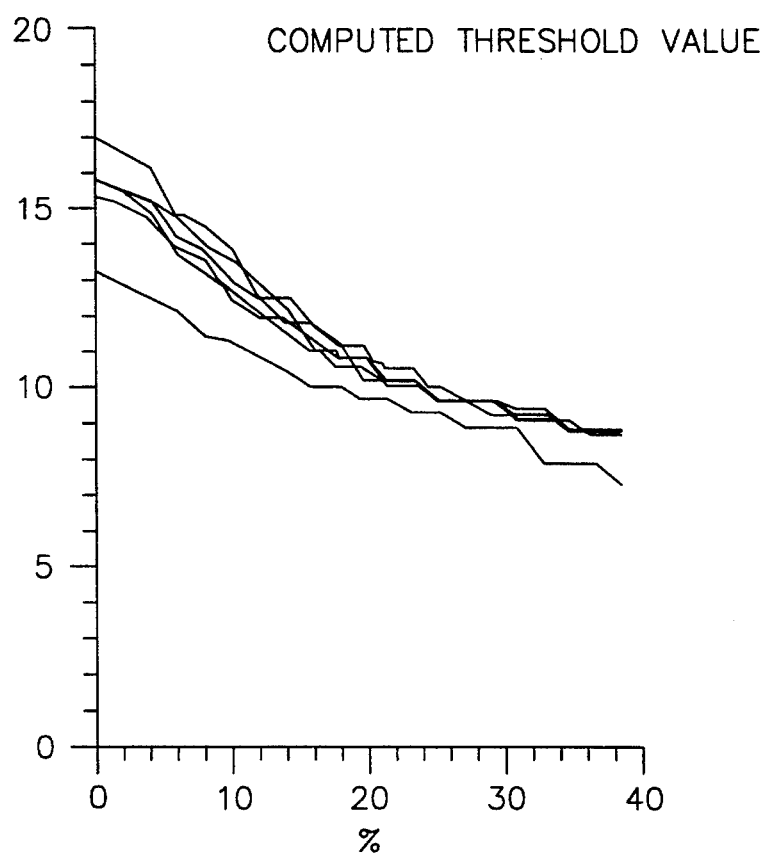
FIG. 12 is a graph showing computed threshold values versus the percentage of bright points discarded from consideration in determining the feature picture threshold.
Figure 13:
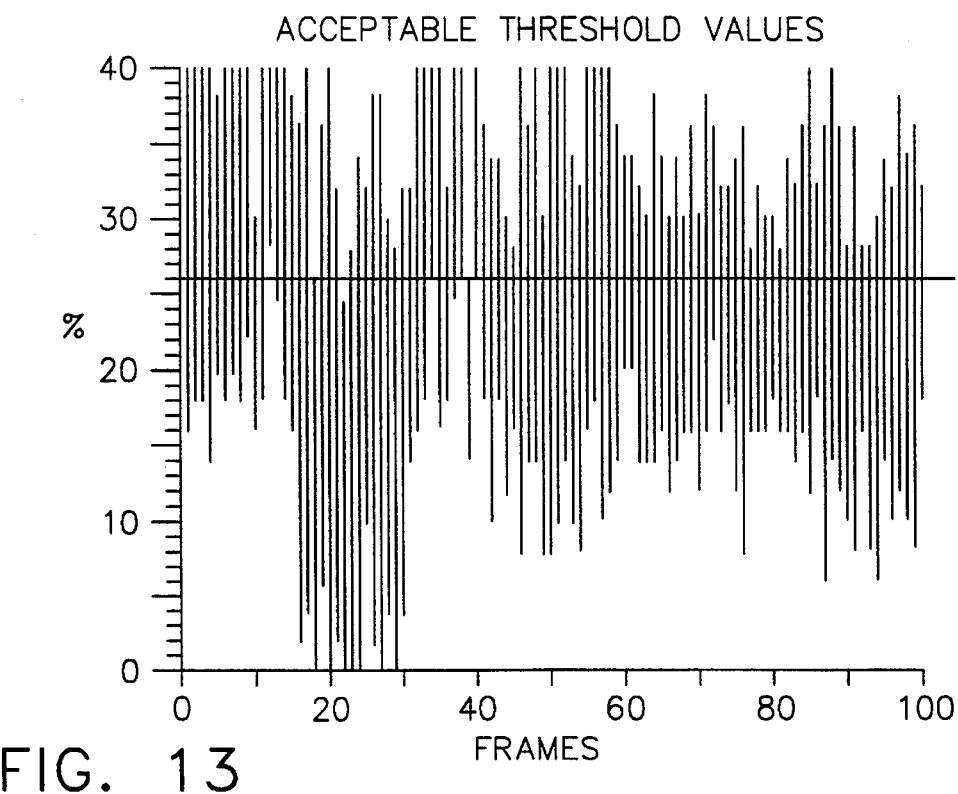
FIG. 13 is a graph of statistical testing of processed video images based on the percentage of bright points discarded.

The selection of the percentage of the discarded bright points in this process is not critical if the selection of the final threshold value is obtained, as it is here, from a processed histogram in which the slope of the line is dependent solely upon the dark regions. In selecting the 26% value, a statistical analysis was performed on 100 different images. FIG. 12 illustrates computed threshold values resulting from discarding between 0% and 40% of the brighter points. Each line within the graph of FIG. 12 represents one picture. FIG. 13 is the statistical result of testing 100 pictures based on acceptance as judged by human eyes. Each vertical line represents the range of percentage discarded brighter points which produced a binary picture which was judged acceptable. The 26% horizontal index line represents the mean value of percentage discarded points for the statistical sampling. In the example, 96% of the computed threshold values were deemed acceptable when discarding 26% of the brighter points. Additional statistical information, or different application specific statistical analysis may produce a different level.

Figure 14:
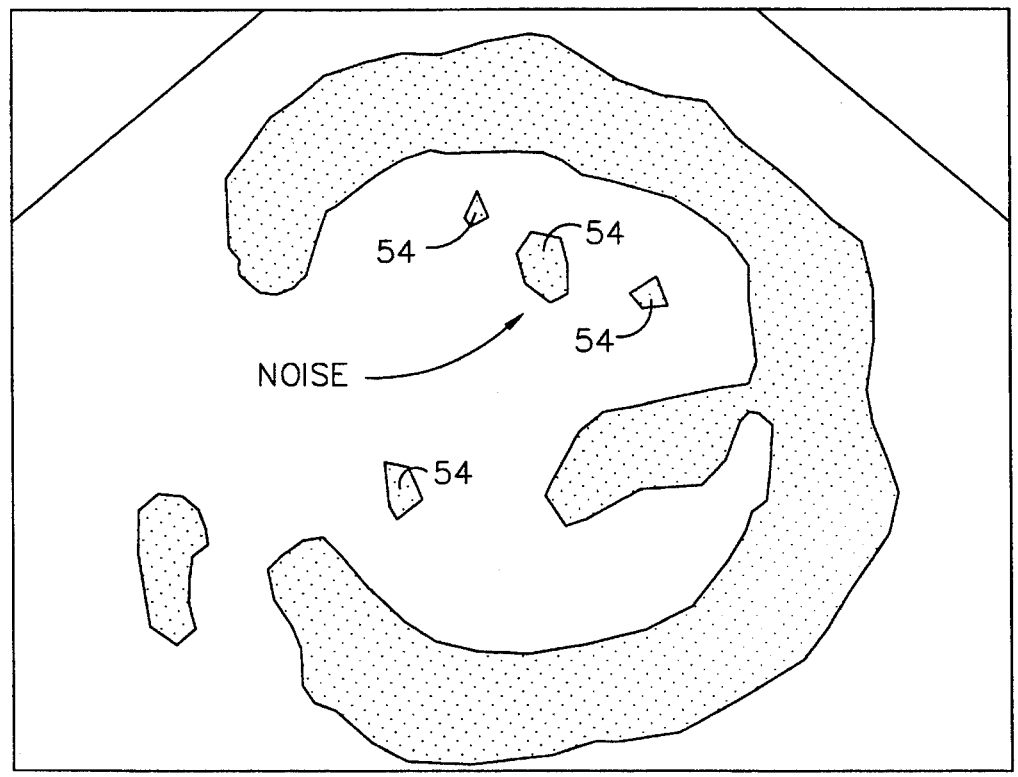
FIG. 14 is a diagrammatic illustration of the feature picture, showing noise blobs.

The second step of the contour extraction stage as it applies to the left ventricle is the LV region segmentation and center finding. Before undertaking segmentation and center finding, a noise cleaning operation is required. Referring to FIG. 14, an image point is considered noise if it belongs to a small "blob" or region 54. At this noise deletion step, a region growing algorithm is used to determine the connected points of a blob and to compute its size. The small blobs are deleted, because they are most likely caused by noise signals.

Figures 15, 16, 17:
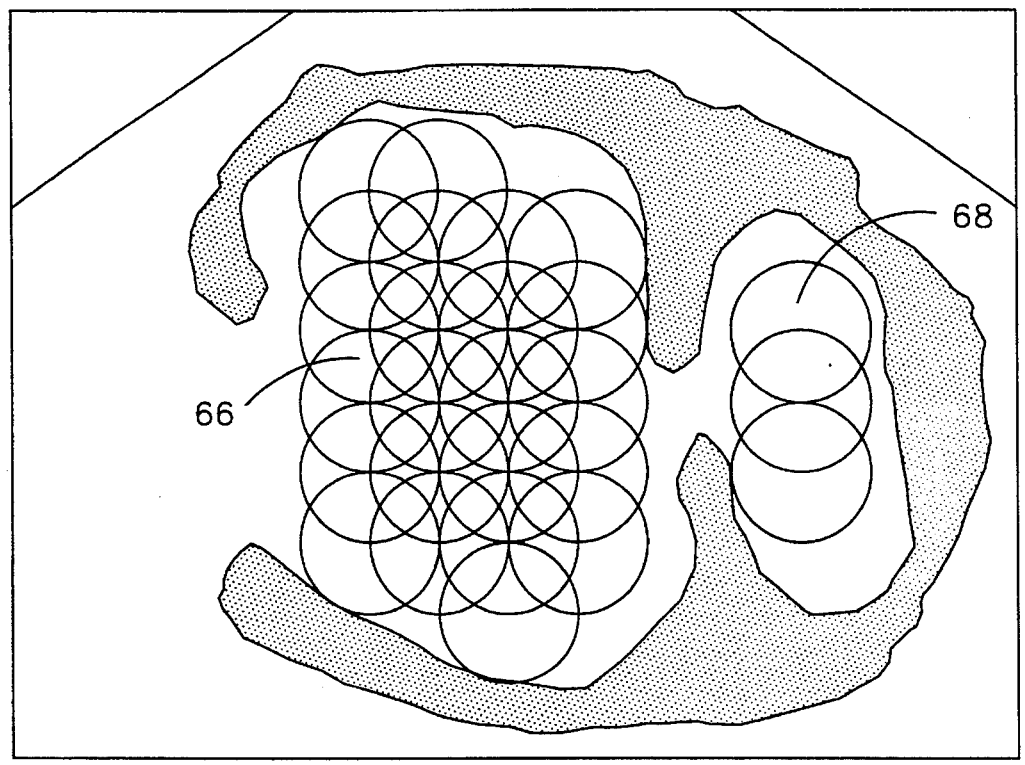
FIG. 15 is a diagrammatic illustration of four points adjacent a seed point.
FIG. 16 is a diagrammatic illustration of the feature picture with circles modelled in the internal LV region.
FIG. 17 is a diagrammatic representation of the grid points used as centers for modelling circles.

The region growing algorithm is a process that begins by "planting" a seed, and then expanding this seed into its surrounding neighborhood until all of the connected pixels are processed. This is an efficient algorithm for tracing connected parts. It is useful in distinguishing different regions and in determining the size of every separated region. The algorithm is as follows:

1. Sequentially search for a "bright" (i.e., first predetermined gray scale value) and non-processed point as a seed point.
2. when found, push this seed point onto a mathematical stack.
3. Remove one seed point from the stack to examine.
4. Check the four adjacent points of the popped seed point. (FIG. 15 illustrates the four adjacent points as circles surrounding the seed point illustrated as an "X".) If any of the four adjacent points are bright, and have not been processed, push each such point onto the stack.
5. Mark the popped point to indicate that it has been processed.
6. Repeat steps 3–5 until the stack is empty. When the stack is empty, one separated region has been processed. Label all of the marked points as members of that region.
7. Repeat steps 1–6 until no bright non-processed point is found at step 1. When none is found, the entire feature picture has been processed.

A counter can be included in the region growing algorithm to count the size of each region while it is being processed. If the number of points within a bright region is below a predetermined quantity, that region is considered as a noise blob. The gray scale levels of all of the points of a nose blob region are set to black, thereby deleting the noise region. In that preferred embodiment, regions having fewer than 20 points were identified as noise blobs.

Next, the center of the LV region can be determined. In order to find this center, it is necessary to determine the internal region of the LV correctly. A problem with accurately identifying the internal region of the LV is that due to signal drop out, the boundary at both sides of the region may be missing. This means that the internal LV region may be connected with the background or other external regions. In accordance with the method of the present invention, the internal region is delineated by locating small geometric shapes, such as circles, in the dark or black regions (i.e., those set to the second predetermined gray scale level) of the feature picture, subject to processing rules, so as to isolate the internal region from the background regions. Although in the preferred embodiment the small testing geometric shapes are identified as circles, a true circle cannot be modeled due to the orthogonal nature of the location of the pixels. For that reason, squares actually result from attempting to model circles.

Referring to FIG. 16, an example of an internal LV region modeled with circles is shown. The centers of the circles are located at respective grid points which correspond to pixel locations. In the preferred embodiment, in order to speed up processing, the grid points are arranged in rows and columns, separated from each other horizontally and vertically by three pixels as shown in FIG. 17. The grid covers the entire feature picture, although only the grid points which are black are considered as possible centers for circles.

The algorithm for determining whether a circle can be located about a particular grid point is based on two rules. First, the circle must not intersect with any bright regions. This means that none of the points on or within the circle can be bright. The second rule of the algorithm is that there must be no more than two radial lines of the horizontal, vertical and diagonal lines emanating from the center of the circle which intersect with the window boundary before intersecting with a bright point. This condition is necessary in order to avoid labeling the points outside of the myocardial muscle regions as internal LV chamber points. All of the pixels inside of the circles whose center points satisfy these two conditions of the algorithm are marked and segmented into regions. The largest of these regions is considered as the internal region, and set equal to a third predetermined gray scale level. Although the feature picture is a binary picture, it may include different gray scale values. For example, the determination of a pixels gray scale level may simply be zero or not zero. If there is a range of gray scale values in the not zero set, the different levels may be used as region identifiers. In the preferred embodiment, the third predetermined gray scale level is higher than the first predetermined gray scale level, producing a brighter internal region than the muscle region. This difference in level between these two points is not critical, so long as the regions are defined and distinguished. In the preferred embodiment, the gray scale levels are used to distinguish regions.

Figure 18:
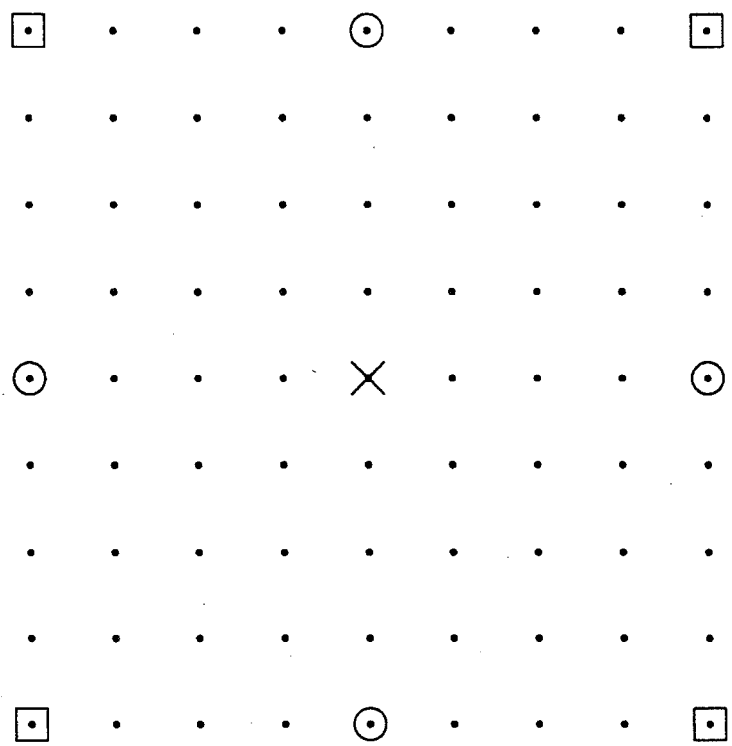
FIG. 18 is a diagrammatic representation of a radius of four pixels in eight directions from a center point.

To effect the testing of the circles, specific procedures are followed. First, the radii for the circles must be selected. A large radius is good for separating two adjoining regions, but is sensitive to noise. For example, if some noise remains within the internal region, the internal region may actually be separated into two regions by a larger radius testing circle. The radius used in the preferred embodiment of the present invention is four pixels. As mentioned above, squares are actually utilized in the preferred embodiment rather than circles. Referring to FIG. 18 which diagrammatically illustrates an array of pixel points, the center of a hypothetical "circle" i.e., a square, is shown marked with an X at the center of the array. In both the vertical and horizontal directions, the outer edge of this geometric shape is indicated by circles located four pixels from the center. In addition to the horizontal and vertical directions, the diagonal directions are also used to define the outer boundary of this geometric shape, the diagonals being located 45° from the vertical or horizontal. In this case, the radius along a diagonal is also four pixels. This "radius" is physically longer than the four pixel radius in the horizontal or vertical directions. These four points are those identified with a square around the pixel point. Thus, as shown by FIG. 18, the resulting geometric shape of the "circle" with a "radius" of four pixels is actually an eight pixel by eight pixel square.

Figure 19:
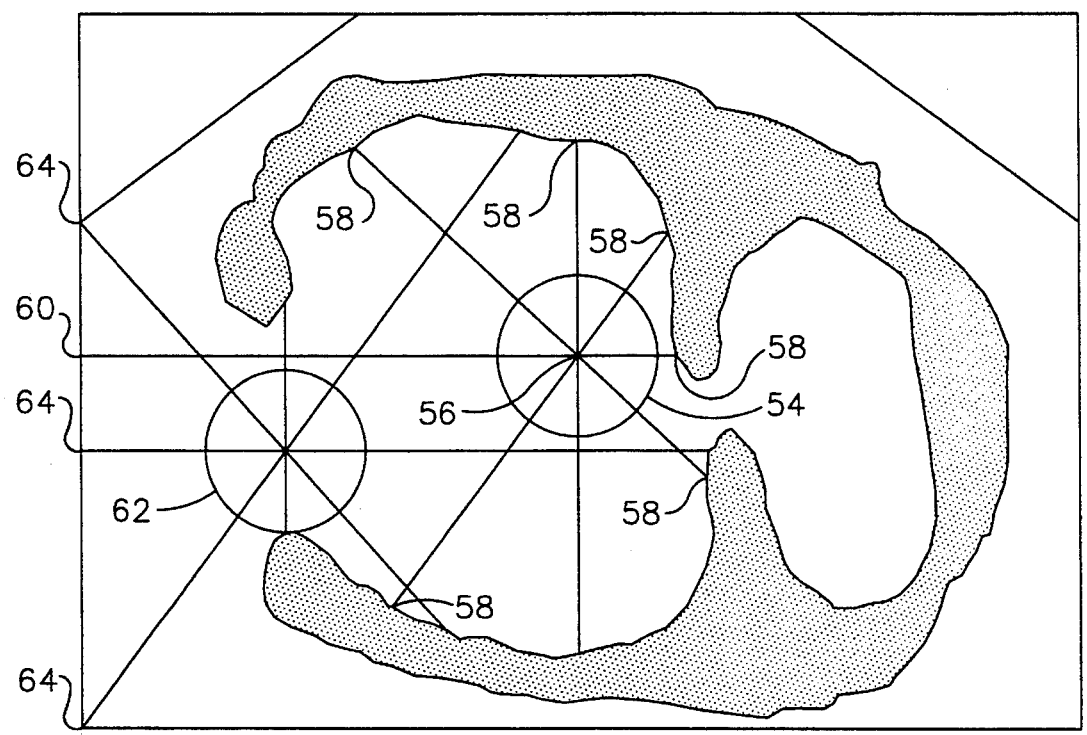
FIG. 19 is a diagrammatic illustration of a feature picture with two circles modelled within the internal LV region.

To implement the two tests of the algorithm to determine whether a "circle" can be fit around the grid point, the eight radial directions are examined. Referring to FIG. 19, there is shown a test "circle" 54 having eight radial lines emanating from its center 56. In sequence, each radial line is expanded outwardly from center 56 until it either intersects with a bright point, such as at points 58, or at the window boundary 60. If a bright point 58 is intersected, the length of the line is tested against the preselected radius, in the preferred embodiment four pixels. If the length is greater than the preselected radius, the next radial line is examined. If the length is less than the preselected radius, then a "circle" cannot be located about grid point 56. If a boundary point 60 is reached, it is noted by the system and the next radial line is considered.

Circle 54 of FIG. 19 has only one radial line which intersects the window boundary at point 60. Therefore, circle 54 also meets the second condition of the algorithm that no more than two radial lines intersect the boundary window. Circle 62 however is shown as having three radial lines which intersect the window boundary at points 64. Although the radius condition is met for circle 62, the window boundary intersection condition is not, and "circle" 62 cannot be located as shown. If a "circle" may be located about a grid point, then all pixels within the boundaries of the "circle," i.e., the square as defined by FIG. 18, are marked. Once all of the grid points have been considered, then each marked pixel is subjected to the region growing algorithm described above, to separate the marked pixels into connected regions.

As shown in FIG. 16, there are two regions, large region 66 and small region 68. Using the region growing algorithm described above, all of the marked points within large region 66 will be identified as belonging to one region, as will all of the marked points within small region 68. Once the black regions have been identified, the largest of the regions is defined to be the internal region of the left ventricle, and the gray scale level of all pixels therein set equal to the third predetermined gray scale level.

Once the internal region has been identified, its center can be found by computing the center of gravity of all of the marked points of the identified internal region. This may be calculated according to the following formulas:

$$X_c = 1/n \times (X_1 + X_2 + X_3 + \ldots + X_n)$$

$$Y_c = 1/n \times (Y_1 + Y_2 + Y_3 + \ldots + Y_n)$$

Where n is the number of total pixels within the identified internal region;

$(X_c, Y_c)$ are the coordinates of the computed center of the internal region; and $(X_i, Y_i)$ are the coordinates of one pixel, where i is from 1 to n.

The next step of the contour extraction stage is the enhancement of the feature picture to further improve the contour detection and closing which follows. Up to this point, only the feature picture has been thresholded as described above. At this step, the original full size windowed picture, which contains the actual boundary information and unaltered pixel gray scale levels, is thresholded and logically ORed with the feature picture in order to enhance the feature picture. A multiple local threshold algorithm is developed because no single global threshold value will work for the entire original picture.

Figure 20:
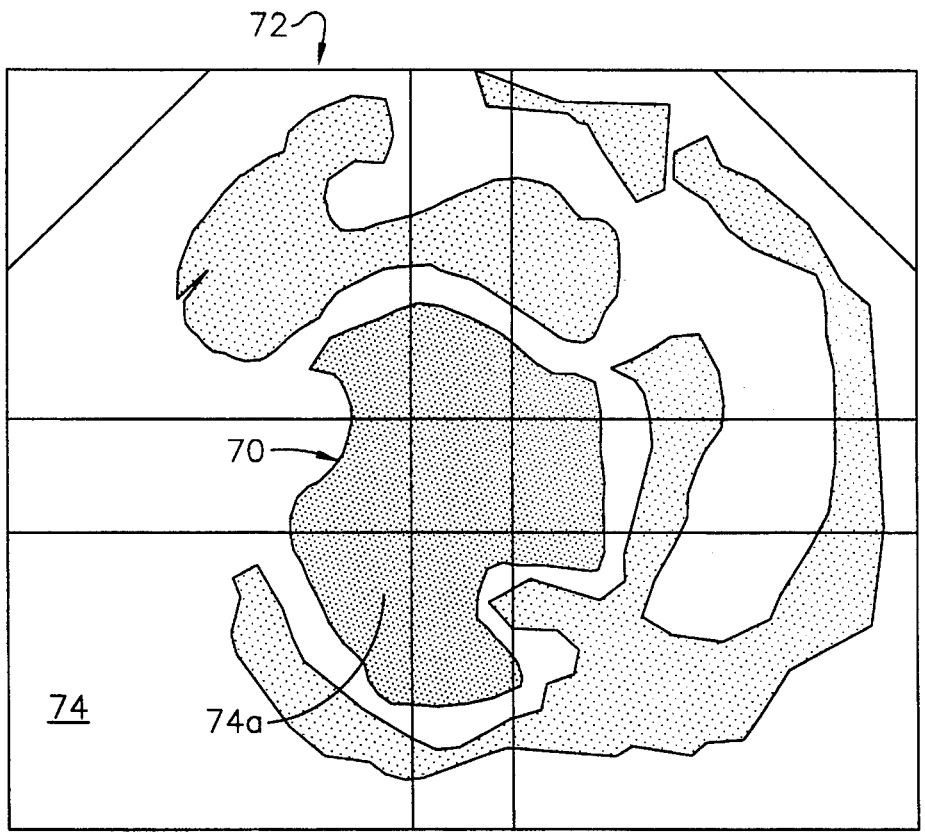
FIG. 20 is a diagrammatic illustration of a reduced size original picture divided into nine sub-regions.
Figure 21:
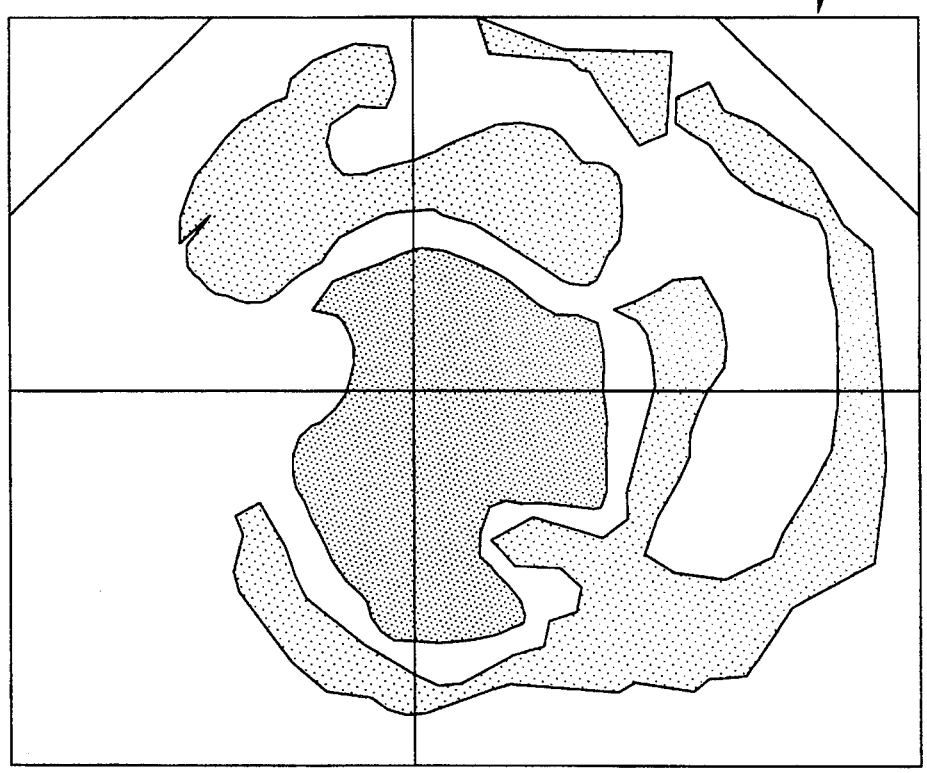
FIG. 21 diagrammatically illustrates a reduced size original picture divided into four sub-regions.

Although other algorithms may be found suitable to enhance the region surrounding the internal region of the feature picture, the following algorithm is utilized in the preferred embodiment. The original picture is reduced to 1/9th of its original size by mapping the center point of each non-overlapping three pixel by three pixel block, along with the respective center point's associated gray scale level into a reduced size of the original picture. This is done in order to be consistent with the size of the feature picture. FIG. 20 diagrammatically illustrates a reduced size original picture having its various gray scale pixels. The internal LV region 70 of reduced size picture 72 is divided into nine sub-regions which each contain internal LV region areas that contain approximately the same number of pixels. This is determined based on the size and the center of the defined internal LV region of the feature picture. The center, number of pixels and internal region boundary is known from the feature picture. This information allows the nine sub-regions shown in the grid of FIG. 20 to be calculated for reduced size original picture 72. If the internal LV region as previously calculated based on the feature picture is too small, the internal LV region sub-areas will not provide significant statistics. In such an event, the reduced original picture 72 is divided into only four sub-regions as illustrated in FIG. 21. Again, these four sub-regions are based on the calculated size, boundaries and center of the internal LV region from the feature picture. In the preferred embodiment, if the internal region contained fewer than 180 pixels, only four sub-regions were used.

Referring again to FIG. 20 a local threshold value for each sub-region is selected based on the largest gray scale value of the internal LV region sub-area. The internal LV region sub-area is that portion of the internal LV region, as determined based on the feature picture, which falls within that sub-region. Thus, for example, sub-region 74 of FIG. 20 contains internal LV region sub-area 74a of internal region area 70. The local threshold value for sub-region 74 is selected such that it is slightly larger than the largest gray scale level within internal LV region sub-area 74a. A different local threshold is selected which is unique to each sub-region.

Within each sub-region, all pixels having a gray scale level less than the threshold level for that sub-region are set equal to zero, while all pixels having gray scale levels greater than the threshold point are set equal to a fourth predetermined gray scale level. In the preferred embodiment, the first and fourth predetermined gray scale levels are equal, since each region so marked corresponds to the myocardial muscles. By setting the local threshold value for each sub-region slightly larger than the largest gray scale level of the internal LV region sub-area within that sub-region, the method insures that all points within the internal LV region on the reduced size original picture will be set equal to zero.

The resulting thresholded binary image of the reduced original picture is then logically ORed with the binary feature picture. In this step, if a particular pixel is equal to the first or fourth predetermined gray scale level in either the feature picture or in the binary reduced original picture, then that pixel is set equal to a fifth predetermined gray scale level in the feature picture. In the preferred embodiment, the first and fifth predetermined gray scale levels are equal. The overall effect of this enhancement of the feature picture is that the outer muscle regions have become more clearly connected to one another.

The next step within the contour extraction stage is the region based contour curve generation. At this point in the processing, the actual LV contour curves should be near the outside of the internal region. The concept in this stage is to dilate the internal region to obtain an expanded internal region, which should contain the actual LV contour points. However, the feature picture at this point contains too much information to be efficiently processed. Since only the boundaries around the internal region are of interest, this step generates and separates those boundaries.

Figure 22:
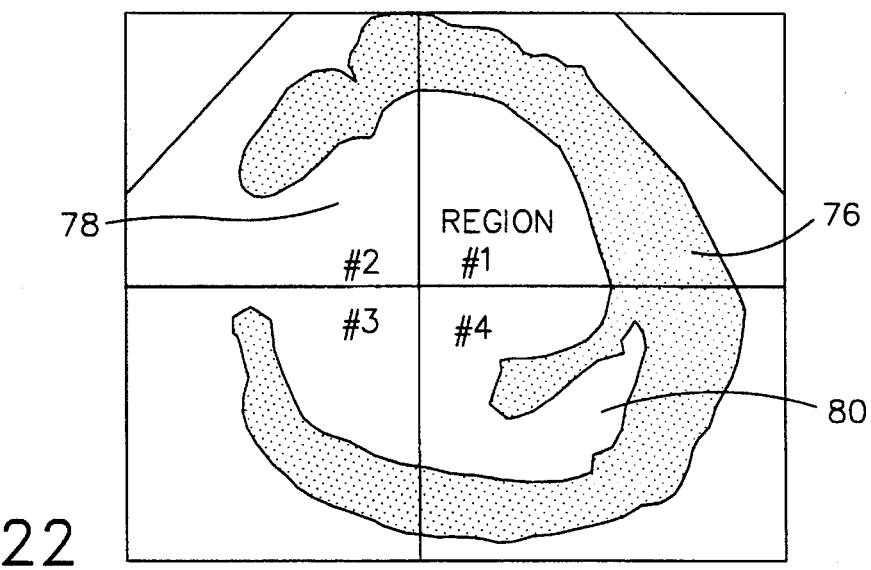
FIG. 22 is a diagrammatic illustration of the feature picture showing four quadrants for dilation.

First, the boundary pixels of the predilation internal LV region are identified. Since the feature picture is primarily binary at this time period and since the internal region is surrounded by a black boundary, the edge may be easily detected and identified. Next, the feature picture is divided into four regions, as illustrated in FIG. 22. It is noted that for clarity the myocardial tissue 76 is shown dotted although in the actual picture of the preferred embodiment it is light with a dark layer between it and internal LV region 78. The internal region 78 is dilated by marking the eight connected neighboring pixels of the previously identified boundary points of the internal region 78. This represents one expansion layer. The number of expansion layers is predetermined for each of the four quadrant regions shown in FIG. 22. For example, because a cave 80 is anticipated to exist as shown in FIG. 22, more layers are added in quadrant four in order to dilate internal region 78 far back into cave 80. Any of the eight neighbors of the boundary pixel which are part of the myocardial muscle, as represented by pixels having the fifth predetermined gray scale level are not changed. Subsequent expansion layers are added outwardly, building outwardly from the previously marked neighboring points. In the preferred embodiment of the present invention, twelve layers were used in region one, two and three, while twenty-two layers were used in region four in order to fill the cave. This provided acceptable results and adequate expansion of the internal region.

After all of the expansion layers have been added to the internal region, the outer boundary of the expanded internal region is determined. Since during the expansion, each expansion layer was marked, the boundary may be determined based on the marked pixels versus unmarked pixels. In the preferred embodiment these pixels were marked, in part, by setting their gray scale levels equal to match the internal LV region.

The final stage of the method of the present invention is knowledge based contour following. Because of the high noise level and the lack of certain boundary signals in the two dimensional image, the boundary defined in the region based contour curve generation step is most likely disconnected and incomplete. Additional interpolation is required to form a meaningful closed contour even after the center or contour edges are determined. The present method incorporates apriori assumptions and knowledge about the images.

Figure 23:
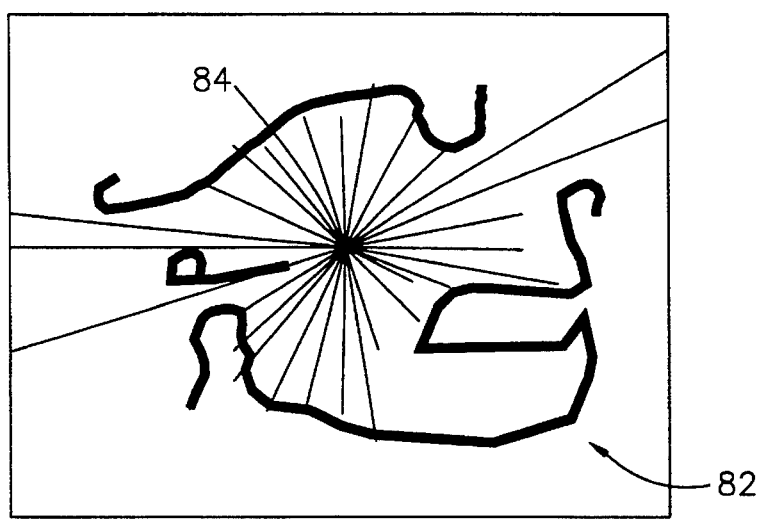
FIG. 23 is a diagrammatic illustration of the feature picture showing discontinuous irregular boundaries.
Figure 24:
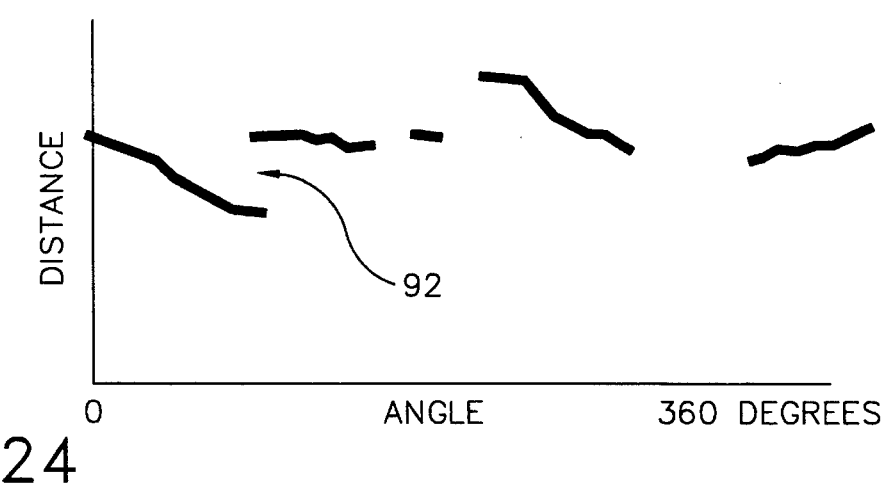
FIG. 24 is an angular position versus distance from center plot of the discontinuous irregular boundaries of the feature picture.

In order to apply these assumptions and knowledge, as will be described later, additional processing of the boundary is necessary. Referring to FIG. 23, discontinuous irregular boundaries are generally shown at 82. At this point, in the procedure the feature picture consists of these boundaries 82 and the center location of the internal region 84. Two steps are taken at this time in order to generate a polar relationship based on the distance between the discontinuous boundaries 82 and center 84 at 128 angular locations originating at center 84. FIG. 24 is the distance from center versus angular displacement, measured clockwise from the horizontal radial lines starting from center to the right. FIG. 24 illustrates the discontinuities present in boundaries 82. It is noted that a circle produces a straight horizontal line when analyzed similarly.

A sequence of processing steps which are based on the distance angle plot illustrated in FIG. 24 is carried out to ensure that the contour is followed, linked and smoothed properly. Knowledge about echo cardiographic images are associated with the features presented in the distance-angle plot to aid the noise cleaning, contour edge detection and contour following functions. Some exemplary abstracted knowledge about the left ventricle and two dimensional transesophageal echocardiography images are summarized below:

(1) The image is sector shape.

(2) The LV is approximately centered in the echo images.

(3) Muscle tissues have brighter intensity and the cavity has darker intensity.

(4) The myocardium wall is relatively thick.

(5) One or two papillary muscles may be present.

(6) Papillary muscles may be attached to the wall (shown as protrusions), or detached from the wall (shown as blobs within the LV).

(7) Wall protrusions may be due to the papillary muscles or trabeculation of the wall.

(8) The orientation of the LV is relatively fixed in two-dimensional transesophageal echocardiographic images.

(9) One papillary muscle is on top of the image, and the other is located at the right bottom of the image.

(10) Papillary muscles are approximately 120° apart with respect to the center. They may not appear distinctly in the images.

(11) The size of the LV dark region is relatively large within the image.

(12) The LV has an overall round shape except on regions around the papillary muscle.

(13) The image gray scale values vary with imaging control and quality.

(14) The right ventricle may appear as a dark blob on the left or on the left bottom part of the image.

(15) Contour edges which are perpendicular to the direction of the echo beam should be clearly visible.

(16) Predominant edges should be approximately perpendicular to the beam direction. Therefore, predominant edges are relatively parallel to each other and may overlap.

(17) Contour edges parallel to the beam direction are likely to be missing.

(18) The separation wall between the right ventricle and left ventricle is on the left of the image and may not be shown.

(19) It is likely that the wall on the top portion of the right side of the image will be missing.

Figure 25:
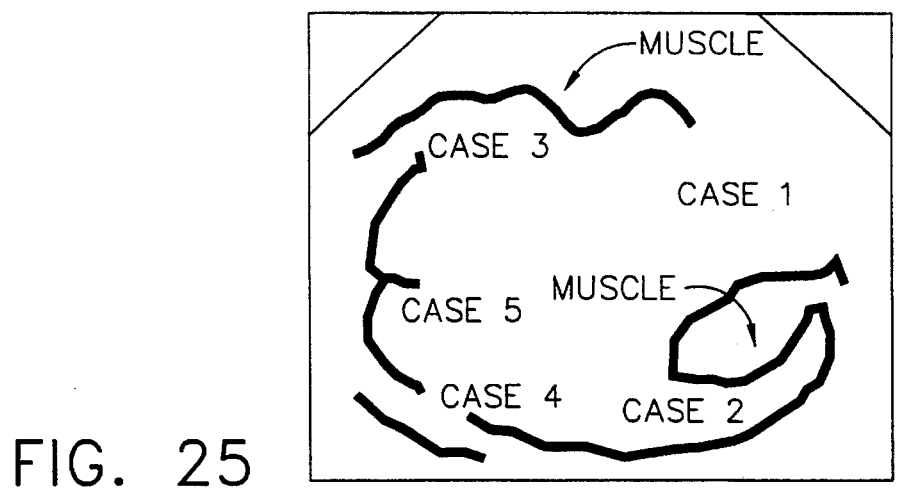
FIG. 25 is a diagrammatic illustration of the five major cases of boundary irregularities.

FIG. 25 illustrates the five major cases of boundary irregularities which need to be handled based on a priori knowledge. In Case 1, a large portion of the edge is missing. Case 2 consists of a cave located behind one of the papillary muscles. Case 3 is when the end of two edges overlap but are not connected together. Case 4 shows a discontinuity in the boundary with an edge behind both of the "loose" ends. Case 5 is due to noise points immediately adjacent the edge, causing a spike as illustrated.

Based on knowledge of the five major cases of boundary irregularities, and the observation set forth above, some specific rules for contour following are encoded into the processing algorithm, as listed below.

1. Noise edge removal. If the length of an edge is short, and there is a long edge behind it, it is most likely a noise edge.
2. There may be a small muscle which causes a triangular shape at the top of the LV contour, as shown at the top of FIG. 25.
3. There may be long portion of the contour missing at the right or left side, which needs to be interpolated (Case 1, FIG. 25).
4. There may be a cave at the right or bottom part which needs further processing (Case 2, FIG. 25).
5. The outer contour of the cave is potentially perpendicular to the radial line eminenting from the center of the internal region.
6. There may be two edges overlapping (Case 3, FIG. 25).
7. There may be some contour boundaries missing with a longer contour boundary behind them (Case 4, FIG. 25).
8. There may be horizontal line noise caused by line scan which is connected to the contour boundaries (Case 5, FIG. 25).
9. If the cave exists and the part of the contour boundary above the cave is lost, the interpolated line should be aligned to the wall of the cave.
10. If there is a small muscle in the left part of the boundary contour nearby is lost, it needs to be interpolated.

Figure 26:
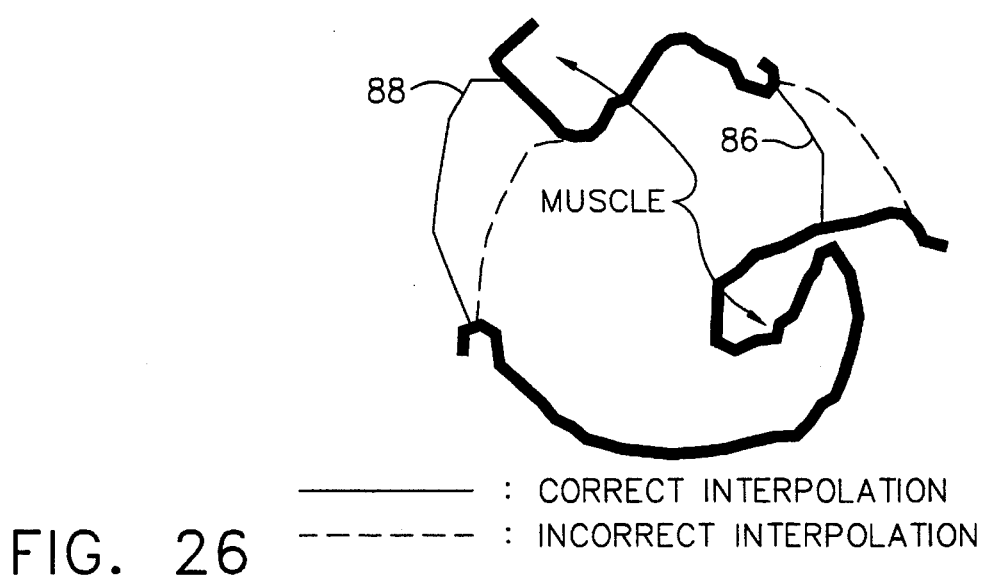
FIG. 26 is a diagrammatic representation of the interpolation of boundary contours.

These last two rules are illustrated in FIG. 26. The boundary contour above the cave is missing. According to rule 9, the correct interpolation for boundary contour portion 86 is as shown, aligned with the wall of the cave at its lower end. At the left of FIG. 26, the left portion of the boundary contour is missing, and is properly interpolated according to rule 10 as shown by boundary contour portion 88.

Figure 27:
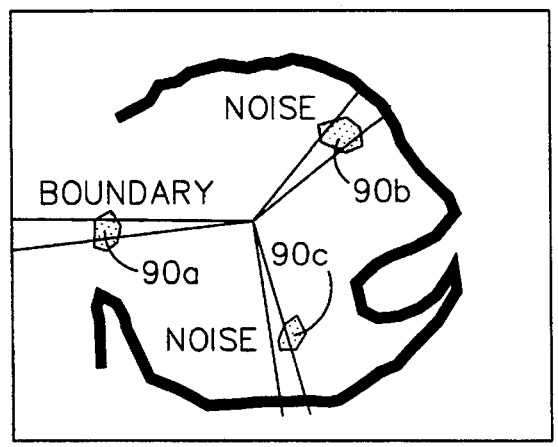
FIG. 27 is a diagrammatic illustration of noise blobs within the contours.

Referring now to FIG. 27, there are shown noise blobs 90*a*, 90*b*, and 90*c*. According to rule 1, blobs 90*b* and 90*c* are removed, because they meet the criteria of a short edge behind which a long edge is located. Noise blob 90*a* does not meet the criteria at this time. It is noted that the length of the noise edge can be computed by the region growing algorithm described above.

Figure 28A:
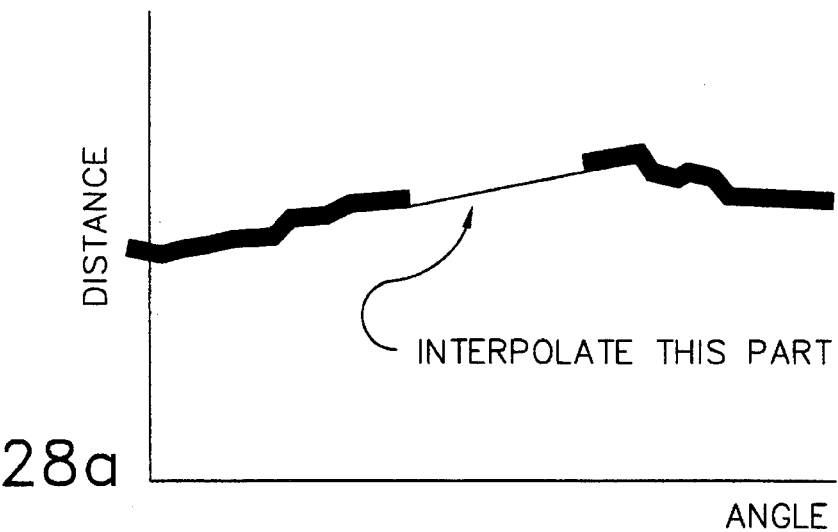
FIGS. 28a, 28b, 28c and 28d are graphs of angular position versus distance from the center which illustrate interpolation for some of the major cases of boundary irregularities.

Referring now to FIG. 28*a*, 28*b*, 28*c* and 28*d*, there are shown the results of the rule based interpolation of Cases 1, 3, 4 and 5 respectively. Case 1, FIG. 28*a* is solved by interpolating the curve connecting the two end points. The curvature of the fitted curve is determined by the distance between the end points and the center. However, if the lost part is near the papillary muscles, the end points sometimes cannot be found because of muscle boundary is parallel to or behind the radial search eminenting from the center. As mentioned above, the end point is traced along the contour based on rule 9.

Figure 28B:
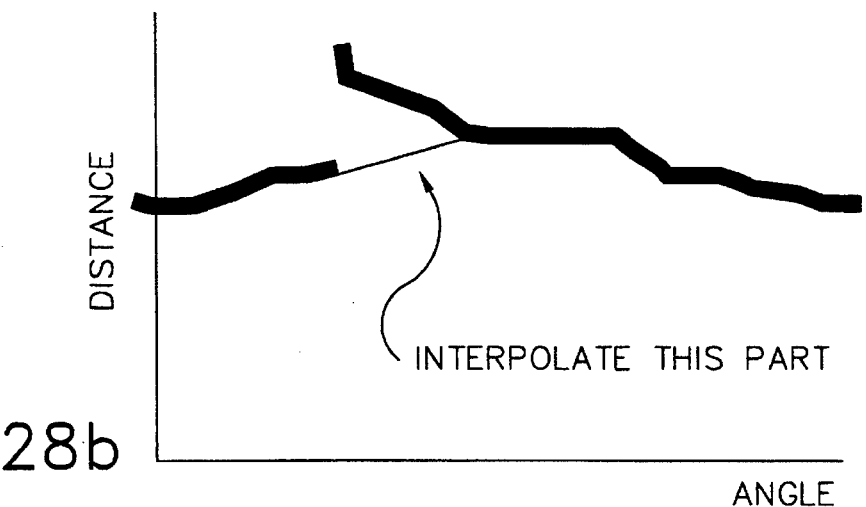

In Case 3, FIG. 28*b*, the plot is characterized by a sharp rise of the curve followed by an abrupt discontinuity change. The two end points are connected by examining the distance versus angle plot and by extending the end point that has a shorter distance to the point on the other edge that has a similar distance value to the center.

Figure 28C:
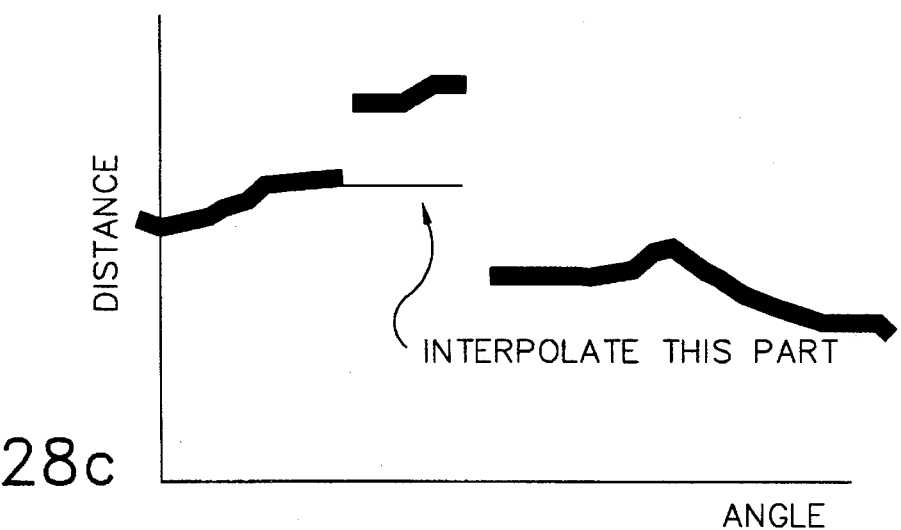

Case 4, FIG. 28*c*, is a short edge on the plot as shown in FIG. 25. The plateau located above the missing continuous portion is removed, and the end points of the curve join together.

Figure 28D:
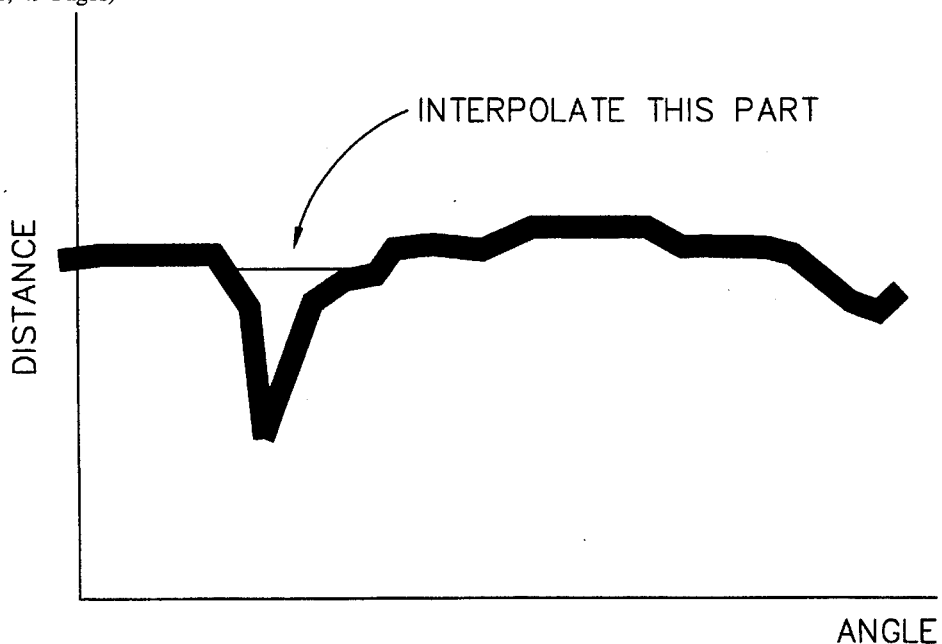

The spiked noise edges in Case 5, FIG. 28*d*, have a similar pattern to Case 3, but are located in an opposite direction thereby causing a sharp decrease in distance. A linking strategy similar to that of Case 3 is used for Case 5 to remove the noise point and connect the edges.

Figure 29:
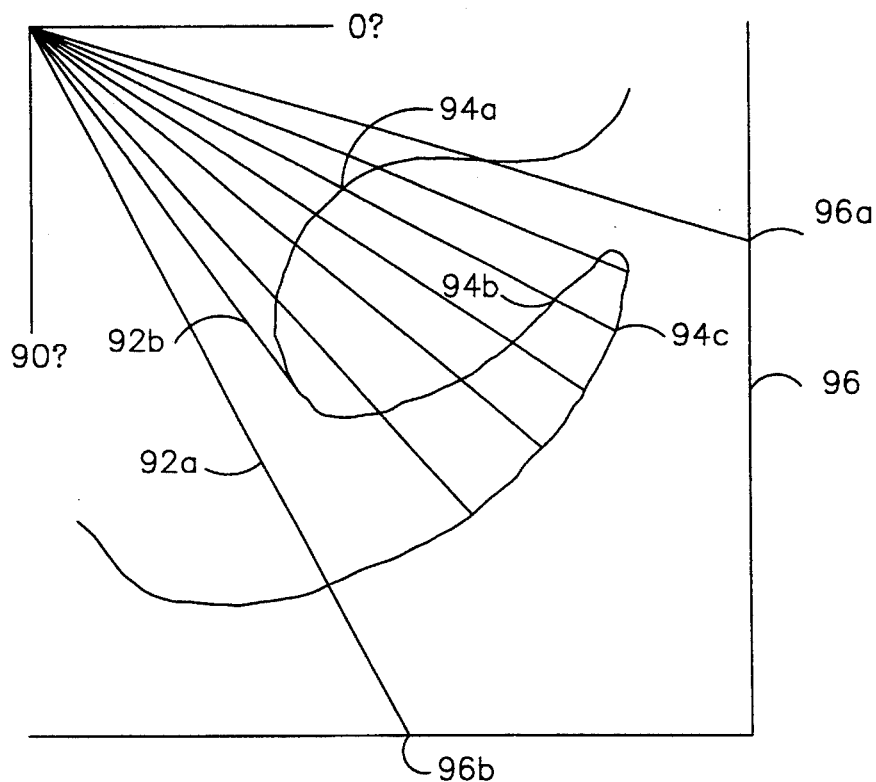
FIG. 29 is a fragmentary diagrammatic illustration of the cave shape and radial lines.

Case 2 is illustrated in FIG. 29, and is established to specifically handle the cave shape. First, based on knowledge about the image, the cave is anticipated to be located within the lower right hand quadrant, wherein the angle is between 0° and 90°. FIG. 24, within the 0° to 90° range, the discontinuity indicated generally at 92 results from the radial distance differences between line 92*a* and 92*b* of FIG. 29. This discontinuity in this quadrant indicates that a cave may be present. Within this region, the radial lines are extended beyond their first point of intersection, for example at 94*a* to search for two other points of intersection along that radial line, 94*b* and 94*c*. For those radial lines at which three intersecting points are found, the two points at the greatest distance represent the cave. The space between corresponding points on sequential radial lines is interpolated as a straight line. Radial lines which reach the boundary 96 such as at points 96*a* and 96*b* after only one intersection indicate the location of the cave to be therebetween.

After interpolating the required boundary points, the result is smoothed. This is accomplished by averaging the radial distance from the center for each angularly disposed point, as illustrated in the distance versus angle graphs, with the radial distance of its two immediate neighbors. This averaging is applied to the entire boundary except for the cave region and other areas where sharp changes exist, such as adjacent the papillary muscles.

The next step in the knowledge base contour following is to search for the actual boundary points on the original picture. The boundary derived so far is not the actual boundary, but is a reduced picture supporting the most logical position of the actual boundary. The actual boundary is searched on the original picture based on the information contained in the finished feature picture.

The search for the actual boundary point is begun by mapping all of the features of the feature picture, such as the center, the 128 radial lines, and the boundary onto the full size original image. Because these features of the feature picture are being expanded back into the center of three pixel by three pixel non-overlapping blocks, the contours of the feature picture when so combined may be shifted from the real contours due to the interpolation in the feature picture.

When the mapping is complete, each actual boundary point is searched for in a small region of N pixels along the respective 128 radial lines centered about the boundary from the feature picture. When N is large, it has the advantage that it can still find the actual boundary points even if the contours of the feature picture have shifted far from the actual contour. However, a large N range may also result in large error if a wrong boundary point is selected. In the preferred embodiment, the actual boundary points were searched for in a region of 15 pixels along each radial line, which is 7 pixels on either side of the feature picture boundary point.

The cave region is searched separately from the other portions of the LV. A smaller search region, where N is equal to 10 pixels is searched to find the contour of the cave. Thereafter the contour is connected with the LV in manner well known in the art.

The search for the actual boundary point is based on the Sobel operator, in accordance with the formula given in FIG. 5 above. Not only is the value of the Sobel operator calculated, but also its direction, according to the formula:

$$\text{angle} = \tan^{-1} \frac{A + 2B + C - G - 2H - I}{C + 2F + I - A - 2D - G}$$

For each candidate point within the range being searched along the radial lines, the Sobel angle and value are calculated. In order to be considered further, the Sobel direction must be outward from the center of the region, i.e., the angle between the Sobel direction and the radial line on which the point lies must be less than 90°. If this test is met, then the Sobel direction for the two points on either side of that candidate point which lie within the range on the radial line are similarly checked. So long as all three Sobel directions are outward from the center of the region, the candidate will be considered further. For the candidate points lying at either end of the range, the Sobel direction is examined only for the adjacent points within the range.

The actual boundary point is selected as the candidate point whose Sobel direction (and the Sobel direction of its neighbors) meet the conditions described above, and has the highest Sobel value of the candidate points meeting the Sobel direction test. This criteria selects the strongest edge point, and checks its neighboring points to avoid the selection of speckle noise.

After all of the edge points are found, median filters are applied to the points to smooth the edge contour. Different filters are used for distinct zones of the image. An 11 point median filter is used in the left half, while a 5 point median filter is used in the right half. This is because the right half is expected to have more actual irregular contours.

At this point in the processing, the real boundary points have been selected and the coordinates of the boundary points are known. The area of the polygon can be calculated according to the following formula:

$$\text{Area} = 1/2 \sum_{K=o}^{N} (X_k Y_{k+1} - X_{k+1} Y_k)$$

Where
$X_k$ and $Y_k$ are the coordinates of a boundary point;
K is from 0 to N; and
N is the number of boundary points.

Thus has been described the preferred embodiment of carrying out the method of the present invention in which an automated highly reliable and accurate system has been described which extracts the boundary of a desired feature, and in particular the left ventricle of the heart, from a video image. The system has a quick response time and can be practically used in a clinical environment.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed:

1. A method for determining the boundary location of an object presented as a video image, the video image comprising a plurality of picture elements known as pixels, each pixel having a respective intensity level, the method comprising the steps of:

(a) generating an original video image of the object;

(b) creating a reduced size feature picture of the original video image of the object;

(c) selecting a threshold value of pixel intensity;

(d) setting the intensity level of all pixels of the feature picture which have a respective intensity level greater than said threshold value equal to a first predetermined intensity level;

(e) setting the intensity level of all pixels of the feature picture which have a respective intensity level less than said threshold value equal to a second predetermined intensity level;

(f) automatically identifying a plurality of adjacent pixels of the feature picture as corresponding to an internal region of the object;

(g) automatically identifying a plurality of internal region boundary pixels as corresponding to the boundary of the internal region;

(h) automatically identifying respective pixels of the original video image which correspond to the internal region boundary pixels identified in step (g); and (i) automatically identifying in the original video image respective object boundary pixels by selecting each respective object boundary pixel from a respective group of candidate pixels which contains a respective pixel identified in step (h).

2. The method of claim 1 wherein step (b) comprises the steps of:

(a) dividing the original video image into non-overlapping groups of pixels;

(b) mapping each group of pixels into a respective single pixel in the feature picture; and (c) assigning each respective single pixel in the feature picture an intensity level based on the intensity levels of the pixels of the respective group of pixels from which said respective single pixel was mapped.

3. The method of claim 2 wherein the step of dividing the original video image comprises dividing the original video image into groups of nine pixels, and wherein the step of assigning an intensity level comprises assigning each respective single pixel an intensity level based on the difference between the maxim and minimum intensity levels of the pixels within the respective group of pixels.

4. The method of claim 1 wherein the step of selecting a threshold value comprises the steps of:

(a) computing a first histogram based on the pixels of the feature picture, said first histogram having an intensity level axis and a quantity of pixels axis;

(b) identifying a plurality of pixels which comprise a first predetermined percentage of the pixels of the feature picture having the highest intensity levels;

(c) eliminating all pixels identified in step (b) from consideration;

(d) computing a second histogram based solely on the remaining pixels of the feature picture which have not been eliminated from consideration, said second histogram having an intensity level axis and a quantity of pixels axis;

(e) determining the highest number of pixels of any given intensity level;

(f) determining the point on the descending side of the curve of the second histogram which corresponds to a second predetermined percentage of the number of pixels determined in step (e);

(g) determining the point on the descending side of the curve of the second histogram which corresponds to a third predetermined percentage of the number of pixels determined in step (e);

(h) determining the point on the intensity level axis of the second histogram which is collinear with the point determined in step (f) and the point determined in step (g); and (i) setting the threshold level equal to the intensity level corresponding to the intensity level of the point determined in step (h).

5. The method according to claim 4 wherein said first predetermined percentage is twenty-six percent.

6. The method according to claim 4 wherein said first predetermined percentage is ninety percent.

7. The method according to claim 4 wherein said first predetermined percentage is ten percent.

8. The method according to claim 4 wherein step (b) includes the step of identifying the eight neighboring pixels of each of the pixels which comprise said first predetermined percentage of pixels having the highest intensity level.

9. The method according to claim 1 comprising, after step (e), the step of deleting video noise from the feature picture.

10. The method according to claim 9, wherein the step of deleting video noise comprises the steps of:

(a) identifying any groups of adjacent pixels which have an intensity level equal to the first predetermined intensity level;

(b) setting the intensity level of each pixel of any group identified in step (a) which consists of fewer than a predetermined number of pixels equal to the second predetermined intensity level.

11. The method according to claim 1 wherein the step of identifying a plurality of pixels as corresponding to an internal region comprises the steps of:

(a) identifying a plurality of grid points corresponding to a plurality of respective pixels of the feature picture;

(b) identifying all pixels on or within a predetermined pattern of pixels adjacent a respective grid point when none of the pixels on or within the respective predetermined pattern of pixels have an intensity level equal to the first predetermined intensity level;

(c) identifying any groups of adjacent pixels which were identified in step (b); and (d) setting the intensity level of each pixel of the largest group of adjacent pixels equal to a third predetermined intensity level.

12. The method according to claim 11 wherein said predetermined pattern of pixels is a rectangle centered about a grid point.

13. The method according to claim 12 wherein the size of said rectangle is nine pixels by nine pixels.

14. The method according to claim 1 wherein the step of identifying a plurality of pixels as corresponding to an internal region comprises the steps of:

(a) identifying a plurality of grid points corresponding to a plurality of respective pixels of the feature picture;

(b) identifying all pixels on or within a predetermined pattern of pixels adjacent a respective grid point when
  (i) none of the pixels on or within the respective predetermined pattern of pixels have an intensity level equal to the first predetermined intensity level, and
  (ii) no more than a predetermined number of a plurality of lines emanating radially from the respective grid point intersect a boundary of the feature picture without passing through a pixel which has an intensity level equal to the first predetermined intensity level;

(c) identifying any groups of adjacent pixels which were identified in step (b); and (d) setting the intensity level of each pixel of the largest group of adjacent pixels equal to a third predetermined intensity level.

15. The method according to claim 14 wherein said predetermined pattern of pixels is a rectangle centered about a grid point.

16. The method according to claim 14 wherein the size of said rectangle is nine pixels by nine pixels.

17. The method according to claim 14 wherein said plurality of radially emanating lines comprises lines emanating in each horizontal, vertical and diagonal direction from the respective grid point.

18. The method according to claim 14 wherein said predetermined number of radially emanating lines is two.

19. The method according to claim 1 wherein the step of identifying a plurality of internal region boundary pixels comprises the steps of:

(a) setting the intensity level of the plurality of adjacent pixels identified in step (f) equal to a third predetermined intensity level;

(b) identifying a plurality of perimeter pixels which form a perimeter of adjacent pixels having an intensity level equal to the third predetermined intensity level;

(c) setting equal to the third predetermined intensity level the intensity level of at least one respective pixel of a plurality of respective pixel groups of eight pixels which surround the respective perimeter pixels; and (d) identifying a plurality of internal region boundary pixels as corresponding to the perimeter pixels.

20. The method according to claim 19 wherein steps (b) and (c) are sequentially performed a plurality of times prior to performing step (d).

21. The method according to claim 1 comprising, after step (f), the steps of:

(a) determining a center location on the feature picture of the center of the internal region of the object based on the respective locations of the plurality of pixels identified as corresponding to an internal region of the object;

(b) determining respective radial distances from the center location to a plurality of respective pixels identified as internal region boundary pixels which lie on a respective one of a plurality of lines emanating radially from said center location;

(c) determining a relationship between the angular position of the respective line and the distance to the respective pixel which lies on the respective line; and (d) interpolating any discontinuities in said relationship based on knowledge of the object.

22. A method of determining a threshold value for processing a video image, the video image comprising a plurality of picture elements known as pixels, each pixel having a respective intensity level, the method comprising the steps of:

(a) computing a first histogram based on the pixels of the video image, said first histogram having an intensity level axis and a quantity of pixels axis;

(b) identifying a plurality of pixels which comprise a predetermined percentage of the pixels of the video image having the highest intensity levels;

(c) eliminating all pixels identified in step (b) from consideration;

(d) computing a second histogram based solely on the remaining pixels of the video image which have not been eliminated from consideration, said second histogram having an intensity level axis and a quantity of pixels axis;

(e) determining the highest number of pixels of any given intensity level;

(f) determining the point on the descending side of the curve of the second histogram which corresponds to a second predetermined percentage of the number of pixels determined in step (e);

(g) determining the point on the descending side of the curve of the second histogram which corresponds to a third predetermined percentage of the number of pixels determined in step (e);

(h) determining the point on the intensity level axis of the second histogram which is collinear with the point determined in step (f) and the point determined in step (g); and (i) setting the threshold level equal to the intensity level corresponding to the intensity level of the point determined in step (h).

23. The method according to claim 22 wherein said first predetermined percentage is twenty-six percent.

24. The method according to claim 22 wherein said first predetermined percentage is ninety percent.

25. The method according to claim 22 wherein said first predetermined percentage is ten percent.

26. The method according to claim 22 wherein step (b) includes the step of identifying the eight neighboring pixels of each of the pixels which comprise said first predetermined percentage of pixels having the highest intensity level.

* * * * *

UNITED STATES PATENT AND TRADEMARK OFFICE
CERTIFICATE OF CORRECTION

PATENT NO. : 5,457,754
DATED : October 10, 1995
INVENTOR(S) : Chia Y. Han, et. al.

It is certified that error appears in the above-indentified patent and that said Letters Patent is hereby corrected as shown below:

Column 21, Claim 3, line 6, delete "maxim" and insert therefor --maximum--

Signed and Sealed this

Twelfth Day of December, 1995

Attest:

BRUCE LEHMAN

Attesting Officer

Commissioner of Patents and Trademarks